(12) United States Patent
Soto-Jara et al.

(10) Patent No.: US 7,598,046 B2
(45) Date of Patent: Oct. 6, 2009

(54) USE OF PRION CONVERSION MODULATING AGENTS

(75) Inventors: Claudio Soto-Jara, Friendswood, TX (US); Kinsey Maundrell, Geneva (CH)

(73) Assignee: Laboratories Serono SA, Coinsins (CH)

( * ) Notice: Subject to any disclaimer, the term of this patent is extended or adjusted under 35 U.S.C. 154(b) by 234 days.

(21) Appl. No.: 10/560,978

(22) PCT Filed: Jun. 18, 2004

(86) PCT No.: PCT/EP2004/051170

§ 371 (c)(1),
(2), (4) Date: Jun. 27, 2006

(87) PCT Pub. No.: WO2004/111652

PCT Pub. Date: Dec. 23, 2004

(65) Prior Publication Data

US 2007/0020682 A1    Jan. 25, 2007

(30) Foreign Application Priority Data

Jun. 19, 2003    (EP) ................................. 03101795

(51) Int. Cl.
*G01N 33/53* (2006.01)
*A61K 49/00* (2006.01)
*A61K 39/395* (2006.01)
*A61K 39/00* (2006.01)

(52) U.S. Cl. .......................... 435/7.2; 435/5; 435/40.5; 424/9.1; 424/130.1; 424/139.1

(58) Field of Classification Search ....................... None
See application file for complete search history.

(56) References Cited

U.S. PATENT DOCUMENTS

| | | | |
|---|---|---|---|
| 5,134,121 A | 7/1992 | Mobley | |
| 5,276,059 A | 1/1994 | Caughey et al. | |
| 5,948,763 A | 9/1999 | Soto-Jara et al. | |
| 6,022,683 A | 2/2000 | Poirier | |
| 6,197,972 B1 | 3/2001 | Heeres et al. | |
| 6,355,610 B2 | 3/2002 | Chesebro et al. | |
| 6,369,075 B1 | 4/2002 | Ruggeri et al. | |
| 6,462,171 B1 | 10/2002 | Soto-Jara et al. | |
| 2002/0128175 A1 | 9/2002 | Anantharamaiah | |
| 2002/0154426 A1 | 10/2002 | Lang et al. | |
| 2004/0018554 A1 | 1/2004 | Green | |

FOREIGN PATENT DOCUMENTS

| | | |
|---|---|---|
| WO | 97/14437 | 4/1997 |
| WO | 99/15159 | 4/1999 |
| WO | 01/68710 | 9/2001 |
| WO | 02/04954 | 1/2002 |
| WO | 02/065133 | 8/2002 |
| WO | 03/002533 | 1/2003 |
| WO | 03/005037 | 1/2003 |
| WO | 03/045921 | 6/2003 |
| WO | 2004/043403 | 5/2004 |

OTHER PUBLICATIONS

Zerr et al (1996) Arch. Neurol. 53(12): 1233-8.*
Namba et al (1991) Brain Res. 541(1): 163-6.*
Naslavsky et al (1997) J Biol Chem. 272(10): 6324-31.*
Soto et al (2002) Trends Neurosci. Aug.;25(8):390-4.*
Huang et al (2001) Proc Natl Acad Sci U S A. Jul. 17;98(15):8838-43.*
Baumann et al (2000) Biochem J. Jul. 1;349(Pt 1):77-84.*
Lingappa, V.R. et al.: "Translocations Pausing and the Regulation of Membrane Protein Biogenesis" Membrane Proteins: Structure, Function and Expression Control Kyushu University Press; S. Karger AG, & International Symposium, pp. 93-100 (XP001183818) 1997.
Clavey, V. et al.: "Interaction entre le LDL-recepteur et les Lipoproteines Contenant de l'Apo B"/"Interaction Between the LDL Receptor and the Lipoproteins Containing APOB", Annales D'Endocrinologie, Masson, Paris, France; vol. 52, pp. 459-463 (XP001029970), 1991.
Baumann, Marc H. et al.: "Apolipoprotein E includes a binding site which is recognized by several amyloidogenic polypeptides" Biochemical Journal, (XP002262330), vol. 349, pp. 77-84, 2000.
Diedrich, Jane F. et al.: "Neuropathological changes in scrapie and Alzheimer's disease are associated with increased expression of apolipoprotein E—and cathepsin D in astrocytes" Journal of Virology (XP000443989), vol. 65, No. 9, pp. 4759-4768, Sep. 1991.
Choe, Leila H. et al.: "Apolipoprotein E and other cerebrospinal fluid proteins differentiate ante mortem variant Creutzfeldt-Jakob disease from ante mortem sporadic Creutzfeldt-Jakob disease" Electrophoresis (XP002262331), vol. 23, No. 14, pp. 2242-2246, 2002.
Golaz, Olivier et al.: "Phenotyping of apolipoprotein E using immobilized pH gradient gels for one-dimensional and two-dimensional separations" Electrophoresis (XP009021630), vol. 16, No. 7, pp. 1184-1186, 1995.
Lucassen, Ralf et al.: "In Vitro Amplification of Protease-Resistant Prion Protein Requires Free Sulfhydryl Groups" Biochemistry (XP002262517) vol. 42, No. 14, pp. 4127-4135, 2003.
Enari, M. et al.: "Scrapie prion protein accumulation by scrapie-infected neuroblastoma cells abrogated by exposure to a prion protein antibody", Proceedings of the National Academy of Sciences of USA, National Academy of Science. Washington, US, vol. 98, No. 16, pp. 9295-9299 (XP002959455) Jul. 31, 2001.
Schulz-Schaeffer, Walter J. et al.: "The Paraffin-Embedded Tissue Blot Detects PrP$^{Sc}$ Early in the Incubation Time in Prion Diseases", American Journal of Pathology (XP002262332) vol. 156, No. 1, pp. 51-56, Jan. 2000.

(Continued)

Primary Examiner—Gary B. Nickol
Assistant Examiner—Michelle Horning
(74) Attorney, Agent, or Firm—Oblon, Spivak, McClelland, Maier & Neustadt, L.L.P.

(57) ABSTRACT

The use of Apolipoprotein B, Apolipoprotein E, fragments and mimetics thereof is provided for diagnostic, detection, prognostic and therapeutic applications In prion diseases. More specifically, the invention provides the use of Apolipoprotein B or fragments thereof for modulating or identifying modulators of the prion protein replication which are implicated in the pathogenesis of transmissible spongiform encephalopathics and other prion diseases.

30 Claims, 8 Drawing Sheets

OTHER PUBLICATIONS

Figure 1:
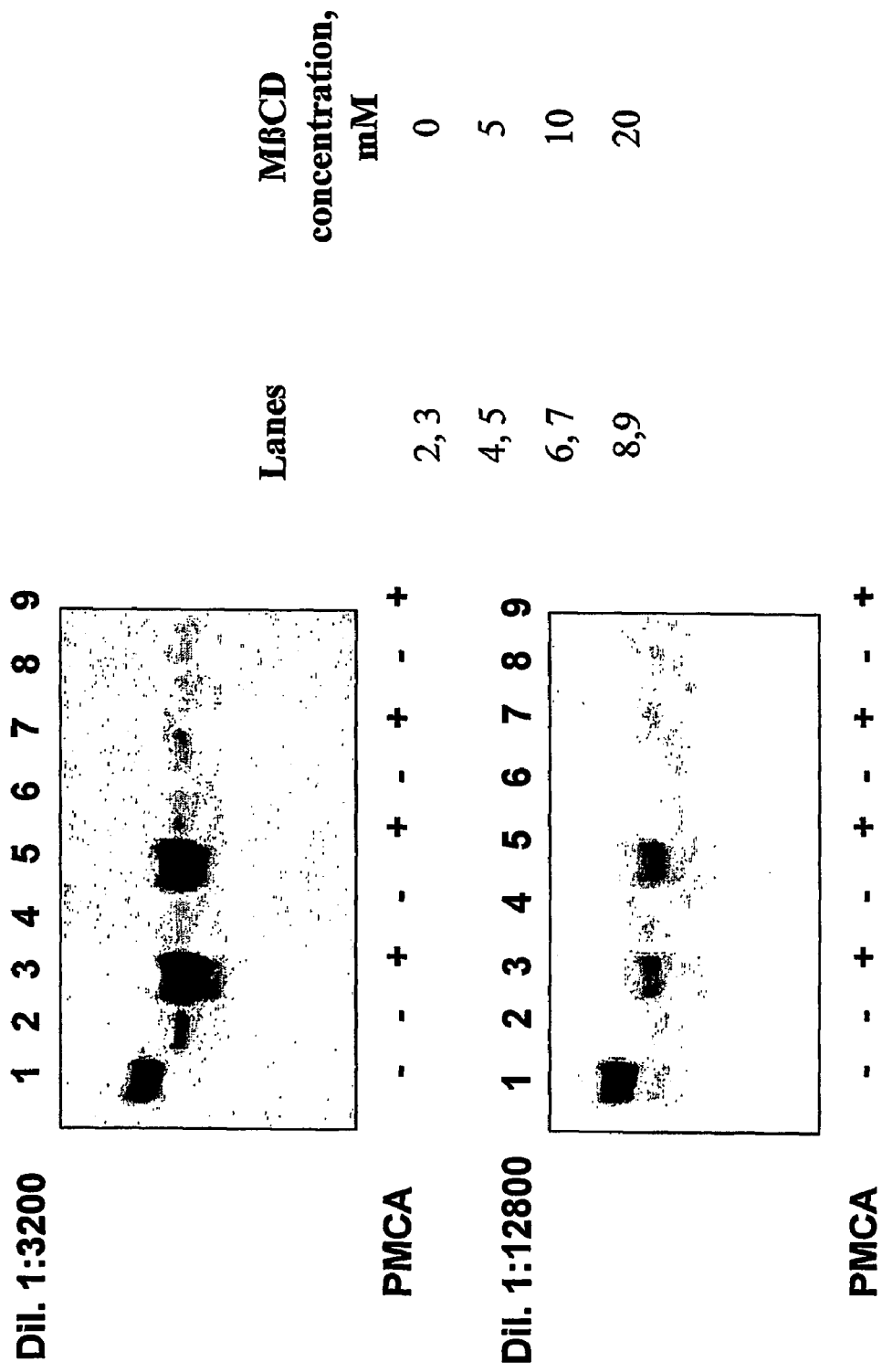

Korth, C. et al.: "Prion (PrP$^{Sc}$)-specific epitope defined by a monoclonal antibody" Nature, MacMillan Journals Ltd. London, GB (XP002069611) vol. 390, pp. 74-77, Nov. 6, 1997.

Aizawa, Yuji et al.: "Amino-terminus truncated apolipoprotein E is the major species in amyloid deposits in Alzheimer's disease-affected brains: a possible role for apolipoprotein E in Alzheimer's disease" Brain Research vol. 768, pp. 208-214, 1997.

Baron, Gerald S. et al.: "Conversion of raft associated prion protein to the protease-resistant state requires insertion of PrP-res (PrP$^{Sc}$) into contiguous membranes" The EMBO Journal vol. 21, No. 5, pp. 1031-1040, 2002.

Bruce, M.E. et al.: "Transmissions to mice indicate that 'new variant' CJD is caused by the BSE agent" Nature, vol. 389, pp. 498-501, Oct. 2, 1997.

Bueler, H. et al.: "Mice Devoid of Prp Are Resistant to Scrapie" Cell vol. 73, pp. 1339-1347, Jul. 2, 1983.

Chabry, Joelle et al.: "Specific Inhibition of in Vitro Formation of Protease-resistant Prion Protein by Synthetic Peptides" The Journal of Biological Chemistry, vol. 273, No. 21, pp. 13203-13207, May 22, 1998.

Choi, Sungshin Y. et al.: "Dissociation of LPL and LDL: effects of lipoproteins and anti-apoB antibodies" Journal of Lipid Research, vol. 38, pp. 77-85, 1997.

Cohen, Fred E. et al.: "Pathologic Conformations of Prion Proteins" Annu. Rev. Biochem., vol. 67, pp. 793-819, 1998.

Fantini, Jacques et al.: "Lipid rafts: structure, function and role in HIV, Alzheimer's and prion diseases" Expert Reviews in Molecular Medicine, pp. 1-22, Dec. 20, 2002.

Hooper, Nigel M.: "Detergent-insoluble glycosphingolipid/cholesterol-rich membraane domains, lipid rafts and caveolae (Review)", Molecular Membrane Biology, vol. 16, pp. 145-156, 1999.

Pan, Keh-Ming et al.: "Conversion of α-helices into β-sheets features in the formation of the scrapie prion proteins" Proc. Natl. Acad. Sci. USA, vol. 90, pp. 10962-10966, Dec. 1993.

Prusiner, Stanley B.: "Molecular Biology of Prion Diseases" Science, vol. 252, pp. 1515-1522, Jun. 14, 1991.

Prusiner, Stanley B.: "Prions" Proc. Natl. Acad. Sci. USA, vol. 95, pp. 13363-13383, Nov. 1998.

Roos, Raymond et al.: "The Clinical Characteristics of Trasnmissible Creutzfeldt-Jakob Disease" Brain, vol. 96, pp. 1-20, 1973.

Saborio, Gabriela P. et al.: "Cell-Lysate Conversion of Prion Protein into Its Protease-Resistant Isoform Suggest the Participation of a Cellular Chaperone" Biochemical and Biophysical Research Communications, vol. 258, pp. 470-475, 1999.

Saborio, Gabriela P. et al.: "Sensitive detection of pathological prion protein by cyclic amplification of protein misfolding", Nature, vol. 411, pp. 810-813, Jun. 14, 2001.

Segrest, Jere P. et al.: "Structure of apolipoprotein B-100 in low density lipoproteins" Journal of Lipid Research, vol. 42, pp. 1346-1367, 2001.

Simons, Kai et al.: "Lipid Rafts and Signal Transduction" Molecular Cell Biology, vol. 1, pp. 31-41, Oct. 2000.

Scott, Michael R. et al.: "Compelling transgenetic evidence for transmission of bovine spongiform encephalopathy prions to humans" Proc. Natl. Acad. Sci. USA, vol. 96, No. 26, pp. 15137-15142, Dec. 21, 1999.

Soto, Claudio et al.: "Prions: disease propagation and disease therapy by conformational transmission" Trends in Molecular Medicine, vol. 7, No. 3, pp. 109-114, Mar. 2001.

Taraboulos, Albert et al.: "Cholesterol Depletion and Modification of COOH-Terminal Targeting Sequence of the Prion Protein Inhibit Formation of the Scrapie Isoform" The Journal of Cell Biology, vol. 129, No. 1, pp. 121-132, Apr. 1995.

Telling, Glenn C. et al.: "Transmission of Creutzfeldt-Jakob disease from humans to transgenic mice expressing chimeric human-mouse prion protein" Proc. Natl. Acad. Sci. USA, vol. 91, pp. 9936-9940, Oct. 1994.

Tsui-Pierchala, Brian A. et al.: "Lipid rafts in neuronal signaling and function" Trends in Neurosciences, vol. 25, No. 8, pp. 412-417, Aug. 2002.

Wang, Xingyu et al.: "Well-Defined Regions of Apolipoprotein B-100 Undergo Conformational Change During Its Intravascular Metabolism" Arterioscler Thromb Vasc Biol., vol. 20, pp. 1301-1308, 2000.

Will R. G. et al.: "A new variant of Creutzfeldt-Jakob disease in the UK" Lancet, vol. 347, pp. 921-925, 1996.

Yamada, Toshiyuki et al.: "Further Characterization of a Monoclonal Antibody Recognizing Apolipoprotein E Peptides in Amyloid Deposits" Annals of Clinical and Laboratory Science, vol. 27, No. 4, pp. 276-281, 1997.

* cited by examiner

SEQUENCE LISTING

<160> NUMBER OF SEQ ID NOS: 6

<210> SEQ ID NO 1
<211> LENGTH: 4563
<212> TYPE: PRT

<213> ORGANISM: Homo sapiens

<400> SEQUENCE: 1

```
Met Asp Pro Pro Arg Pro Ala Leu Leu Ala Leu Leu Ala Leu Pro Ala
1               5                   10                  15
Leu Leu Leu Leu Leu Leu Ala Gly Ala Arg Ala Glu Glu Glu Met Leu
            20                  25                  30
Glu Asn Val Ser Leu Val Cys Pro Lys Asp Ala Thr Arg Phe Lys His
        35                  40                  45
Leu Arg Lys Tyr Thr Tyr Asn Tyr Glu Ala Glu Ser Ser Ser Gly Val
    50                  55                  60
Pro Gly Thr Ala Asp Ser Arg Ser Ala Thr Arg Ile Asn Cys Lys Val
65                  70                  75                  80
Glu Leu Glu Val Pro Gln Leu Cys Ser Phe Ile Leu Lys Thr Ser Gln
                85                  90                  95
Cys Thr Leu Lys Glu Val Tyr Gly Phe Asn Pro Glu Gly Lys Ala Leu
            100                 105                 110
Leu Lys Lys Thr Lys Asn Ser Glu Glu Phe Ala Ala Met Ser Arg
        115                 120                 125
Tyr Glu Leu Lys Leu Ala Ile Pro Glu Gly Lys Gln Val Phe Leu Tyr
    130                 135                 140
Pro Glu Lys Asp Glu Pro Thr Tyr Ile Leu Asn Ile Lys Arg Gly Ile
145                 150                 155                 160
Ile Ser Ala Leu Leu Val Pro Pro Glu Thr Glu Glu Ala Lys Gln Val
                165                 170                 175
Leu Phe Leu Asp Thr Val Tyr Gly Asn Cys Ser Thr His Phe Thr Val
            180                 185                 190
Lys Thr Arg Lys Gly Asn Val Ala Thr Glu Ile Ser Thr Glu Arg Asp
        195                 200                 205
Leu Gly Gln Cys Asp Arg Phe Lys Pro Ile Arg Thr Gly Ile Ser Pro
    210                 215                 220
Leu Ala Leu Ile Lys Gly Met Thr Arg Pro Leu Ser Thr Leu Ile Ser
225                 230                 235                 240
Ser Ser Gln Ser Cys Gln Tyr Thr Leu Asp Ala Lys Arg Lys His Val
                245                 250                 255
Ala Glu Ala Ile Cys Lys Glu Gln His Leu Phe Leu Pro Phe Ser Tyr
            260                 265                 270
Asn Asn Lys Tyr Gly Met Val Ala Gln Val Thr Gln Thr Leu Lys Leu
        275                 280                 285
Glu Asp Thr Pro Lys Ile Asn Ser Arg Phe Phe Gly Glu Gly Thr Lys
    290                 295                 300
Lys Met Gly Leu Ala Phe Glu Ser Thr Lys Ser Thr Ser Pro Pro Lys
305                 310                 315                 320
Gln Ala Glu Ala Val Leu Lys Thr Leu Gln Glu Leu Lys Lys Leu Thr
                325                 330                 335
Ile Ser Glu Gln Asn Ile Gln Arg Ala Asn Leu Phe Asn Lys Leu Val
            340                 345                 350
Thr Glu Leu Arg Gly Leu Ser Asp Glu Ala Val Thr Ser Leu Leu Pro
        355                 360                 365
Gln Leu Ile Glu Val Ser Ser Pro Ile Thr Leu Gln Ala Leu Val Gln
    370                 375                 380
Cys Gly Gln Pro Gln Cys Ser Thr His Ile Leu Gln Trp Leu Lys Arg
385                 390                 395                 400
```

```
Val His Ala Asn Pro Leu Leu Ile Asp Val Val Thr Tyr Leu Val Ala
            405                 410                 415
Leu Ile Pro Glu Pro Ser Ala Gln Gln Leu Arg Glu Ile Phe Asn Met
            420                 425                 430
Ala Arg Asp Gln Arg Ser Arg Ala Thr Leu Tyr Ala Leu Ser His Ala
            435                 440                 445
Val Asn Asn Tyr His Lys Thr Asn Pro Thr Gly Thr Gln Glu Leu Leu
450                 455                 460
Asp Ile Ala Asn Tyr Leu Met Glu Gln Ile Gln Asp Cys Thr Gly
465                 470                 475                 480
Asp Glu Asp Tyr Thr Tyr Leu Ile Leu Arg Val Ile Gly Asn Met Gly
                    485                 490                 495
Gln Thr Met Glu Gln Leu Thr Pro Glu Leu Lys Ser Ser Ile Leu Lys
                500                 505                 510
Cys Val Gln Ser Thr Lys Pro Ser Leu Met Ile Gln Lys Ala Ala Ile
            515                 520                 525
Gln Ala Leu Arg Lys Met Glu Pro Lys Asp Lys Asp Gln Glu Val Leu
530                 535                 540
Leu Gln Thr Phe Leu Asp Asp Ala Ser Pro Gly Asp Lys Arg Leu Ala
545                 550                 555                 560
Ala Tyr Leu Met Leu Met Arg Ser Pro Ser Gln Ala Asp Ile Asn Lys
                565                 570                 575
Ile Val Gln Ile Leu Pro Trp Glu Gln Asn Glu Gln Val Lys Asn Phe
                580                 585                 590
Val Ala Ser His Ile Ala Asn Ile Leu Asn Ser Glu Leu Asp Ile
            595                 600                 605
Gln Asp Leu Lys Lys Leu Val Lys Glu Ala Leu Lys Glu Ser Gln Leu
610                 615                 620
Pro Thr Val Met Asp Phe Arg Lys Phe Ser Arg Asn Tyr Gln Leu Tyr
625                 630                 635                 640
Lys Ser Val Ser Leu Pro Ser Leu Asp Pro Ala Ser Ala Lys Ile Glu
                645                 650                 655
Gly Asn Leu Ile Phe Asp Pro Asn Asn Tyr Leu Pro Lys Glu Ser Met
                660                 665                 670
Leu Lys Thr Thr Leu Thr Ala Phe Gly Phe Ala Ser Ala Asp Leu Ile
            675                 680                 685
Glu Ile Gly Leu Glu Gly Lys Gly Phe Glu Pro Thr Leu Glu Ala Leu
            690                 695                 700
Phe Gly Lys Gln Gly Phe Phe Pro Asp Ser Val Asn Lys Ala Leu Tyr
705                 710                 715                 720
Trp Val Asn Gly Gln Val Pro Asp Gly Val Ser Lys Val Leu Val Asp
                725                 730                 735
His Phe Gly Tyr Thr Lys Asp Lys His Glu Gln Asp Met Val Asn
                740                 745                 750
Gly Ile Met Leu Ser Val Glu Lys Leu Ile Lys Asp Leu Lys Ser Lys
            755                 760                 765
Glu Val Pro Glu Ala Arg Ala Tyr Leu Arg Ile Leu Gly Glu Glu Leu
            770                 775                 780
Gly Phe Ala Ser Leu His Asp Leu Gln Leu Leu Gly Lys Leu Leu
785                 790                 795                 800
Met Gly Ala Arg Thr Leu Gln Gly Ile Pro Gln Met Ile Gly Glu Val
                805                 810                 815
Ile Arg Lys Gly Ser Lys Asn Asp Phe Phe Leu His Tyr Ile Phe Met
```

-continued

```
                820                 825                 830
Glu Asn Ala Phe Glu Leu Pro Thr Gly Ala Gly Leu Gln Leu Gln Ile
    835                 840                 845
Ser Ser Ser Gly Val Ile Ala Pro Gly Ala Lys Ala Gly Val Lys Leu
    850                 855                 860
Glu Val Ala Asn Met Gln Ala Glu Leu Val Ala Lys Pro Ser Val Ser
865                 870                  875                 880
Val Glu Phe Val Thr Asn Met Gly Ile Ile Ile Pro Asp Phe Ala Arg
                885                 890                 895
Ser Gly Val Gln Met Asn Thr Asn Phe Phe His Glu Ser Gly Leu Glu
            900                 905                 910
Ala His Val Ala Leu Lys Ala Gly Lys Leu Lys Phe Ile Ile Pro Ser
            915                 920                 925
Pro Lys Arg Pro Val Lys Leu Leu Ser Gly Gly Asn Thr Leu His Leu
        930                 935                 940
Val Ser Thr Thr Lys Thr Glu Val Ile Pro Pro Leu Ile Glu Asn Arg
945                 950                 955                 960
Gln Ser Trp Ser Val Cys Lys Gln Val Phe Pro Gly Leu Asn Tyr Cys
                965                 970                 975
Thr Ser Gly Ala Tyr Ser Asn Ala Ser Ser Thr Asp Ser Ala Ser Tyr
            980                 985                 990
Tyr Pro Leu Thr Gly Asp Thr Arg Leu Glu Leu Glu Leu Arg Pro Thr
        995                 1000                1005
Gly Glu Ile Glu Gln Tyr Ser Val Ser Ala Thr Tyr Glu Leu Gln
    1010                1015                1020
Arg Glu Asp Arg Ala Leu Val Asp Thr Leu Lys Phe Val Thr Gln
    1025                1030                1035
Ala Glu Gly Ala Lys Gln Thr Glu Ala Thr Met Thr Phe Lys Tyr
    1040                1045                1050
Asn Arg Gln Ser Met Thr Leu Ser Ser Glu Val Gln Ile Pro Asp
    1055                1060                1065
Phe Asp Val Asp Leu Gly Thr Ile Leu Arg Val Asn Asp Glu Ser
    1070                1075                1080
Thr Glu Gly Lys Thr Ser Tyr Arg Leu Thr Leu Asp Ile Gln Asn
    1085                1090                1095
Lys Lys Ile Thr Glu Val Ala Leu Met Gly His Leu Ser Cys Asp
    1100                1105                1110
Thr Lys Glu Glu Arg Lys Ile Lys Gly Val Ile Ser Ile Pro Arg
    1115                1120                1125
Leu Gln Ala Glu Ala Arg Ser Glu Ile Leu Ala His Trp Ser Pro
    1130                1135                1140
Ala Lys Leu Leu Leu Gln Met Asp Ser Ser Ala Thr Ala Tyr Gly
    1145                1150                1155
Ser Thr Val Ser Lys Arg Val Ala Trp His Tyr Asp Glu Glu Lys
    1160                1165                1170
Ile Glu Phe Glu Trp Asn Thr Gly Thr Asn Val Asp Thr Lys Lys
    1175                1180                1185
Met Thr Ser Asn Phe Pro Val Asp Leu Ser Asp Tyr Pro Lys Ser
    1190                1195                1200
Leu His Met Tyr Ala Asn Arg Leu Leu Asp His Arg Val Pro Glu
    1205                1210                1215
Thr Asp Met Thr Phe Arg His Val Gly Ser Lys Leu Ile Val Ala
    1220                1225                1230
```

```
Met Ser Ser Trp Leu Gln Lys Ala Ser Gly Ser Leu Pro Tyr Thr
    1235            1240                1245

Gln Thr Leu Gln Asp His Leu Asn Ser Leu Lys Glu Phe Asn Leu
    1250            1255                1260

Gln Asn Met Gly Leu Pro Asp Phe His Ile Pro Glu Asn Leu Phe
    1265            1270                1275

Leu Lys Ser Asp Gly Arg Val Lys Tyr Thr Leu Asn Lys Asn Ser
    1280            1285                1290

Leu Lys Ile Glu Ile Pro Leu Pro Phe Gly Gly Lys Ser Ser Arg
    1295            1300                1305

Asp Leu Lys Met Leu Glu Thr Val Arg Thr Pro Ala Leu His Phe
    1310            1315                1320

Lys Ser Val Gly Phe His Leu Pro Ser Arg Glu Phe Gln Val Pro
    1325            1330                1335

Thr Phe Thr Ile Pro Lys Leu Tyr Gln Leu Gln Val Pro Leu Leu
    1340            1345                1350

Gly Val Leu Asp Leu Ser Thr Asn Val Tyr Ser Asn Leu Tyr Asn
    1355            1360                1365

Trp Ser Ala Ser Tyr Ser Gly Gly Asn Thr Ser Thr Asp His Phe
    1370            1375                1380

Ser Leu Arg Ala Arg Tyr His Met Lys Ala Asp Ser Val Val Asp
    1385            1390                1395

Leu Leu Ser Tyr Asn Val Gln Gly Ser Gly Glu Thr Thr Tyr Asp
    1400            1405                1410

His Lys Asn Thr Phe Thr Leu Ser Cys Asp Gly Ser Leu Arg His
    1415            1420                1425

Lys Phe Leu Asp Ser Asn Ile Lys Phe Ser His Val Glu Lys Leu
    1430            1435                1440

Gly Asn Asn Pro Val Ser Lys Gly Leu Leu Ile Phe Asp Ala Ser
    1445            1450                1455

Ser Ser Trp Gly Pro Gln Met Ser Ala Ser Val His Leu Asp Ser
    1460            1465                1470

Lys Lys Lys Gln His Leu Phe Val Lys Glu Val Lys Ile Asp Gly
    1475            1480                1485

Gln Phe Arg Val Ser Ser Phe Tyr Ala Lys Gly Thr Tyr Gly Leu
    1490            1495                1500

Ser Cys Gln Arg Asp Pro Asn Thr Gly Arg Leu Asn Gly Glu Ser
    1505            1510                1515

Asn Leu Arg Phe Asn Ser Ser Tyr Leu Gln Gly Thr Asn Gln Ile
    1520            1525                1530

Thr Gly Arg Tyr Glu Asp Gly Thr Leu Ser Leu Thr Ser Thr Ser
    1535            1540                1545

Asp Leu Gln Ser Gly Ile Ile Lys Asn Thr Ala Ser Leu Lys Tyr
    1550            1555                1560

Glu Asn Tyr Glu Leu Thr Leu Lys Ser Asp Thr Asn Gly Lys Tyr
    1565            1570                1575

Lys Asn Phe Ala Thr Ser Asn Lys Met Asp Met Thr Phe Ser Lys
    1580            1585                1590

Gln Asn Ala Leu Leu Arg Ser Glu Tyr Gln Ala Asp Tyr Glu Ser
    1595            1600                1605

Leu Arg Phe Phe Ser Leu Leu Ser Gly Ser Leu Asn Ser His Gly
    1610            1615                1620
```

```
Leu Glu  Leu Asn Ala Asp Ile  Leu Gly Thr Asp Lys  Ile Asn Ser
    1625             1630              1635

Gly Ala  His Lys Ala Thr Leu  Arg Ile Gly Gln Asp  Gly Ile Ser
    1640             1645              1650

Thr Ser  Ala Thr Thr Asn Leu  Lys Cys Ser Leu Leu  Val Leu Glu
    1655             1660              1665

Asn Glu  Leu Asn Ala Glu Leu  Gly Leu Ser Gly Ala  Ser Met Lys
    1670             1675              1680

Leu Thr  Thr Asn Gly Arg Phe  Arg Glu His Asn Ala  Lys Phe Ser
    1685             1690              1695

Leu Asp  Gly Lys Ala Ala Leu  Thr Glu Leu Ser Leu  Gly Ser Ala
    1700             1705              1710

Tyr Gln  Ala Met Ile Leu Gly  Val Asp Ser Lys Asn  Ile Phe Asn
    1715             1720              1725

Phe Lys  Val Ser Gln Glu Gly  Leu Lys Leu Ser Asn  Asp Met Met
    1730             1735              1740

Gly Ser  Tyr Ala Glu Met Lys  Phe Asp His Thr Asn  Ser Leu Asn
    1745             1750              1755

Ile Ala  Gly Leu Ser Leu Asp  Phe Ser Ser Lys Leu  Asp Asn Ile
    1760             1765              1770

Tyr Ser  Ser Asp Lys Phe Tyr  Lys Gln Thr Val Asn  Leu Gln Leu
    1775             1780              1785

Gln Pro  Tyr Ser Leu Val Thr  Thr Leu Asn Ser Asp  Leu Lys Tyr
    1790             1795              1800

Asn Ala  Leu Asp Leu Thr Asn  Asn Gly Lys Leu Arg  Leu Glu Pro
    1805             1810              1815

Leu Lys  Leu His Val Ala Gly  Asn Leu Lys Gly Ala  Tyr Gln Asn
    1820             1825              1830

Asn Glu  Ile Lys His Ile Tyr  Ala Ile Ser Ser Ala  Ala Leu Ser
    1835             1840              1845

Ala Ser  Tyr Lys Ala Asp Thr  Val Ala Lys Val Gln  Gly Val Glu
    1850             1855              1860

Phe Ser  His Arg Leu Asn Thr  Asp Ile Ala Gly Leu  Ala Ser Ala
    1865             1870              1875

Ile Asp  Met Ser Thr Asn Tyr  Asn Ser Asp Ser Leu  His Phe Ser
    1880             1885              1890

Asn Val  Phe Arg Ser Val Met  Ala Pro Phe Thr Met  Thr Ile Asp
    1895             1900              1905

Ala His  Thr Asn Gly Asn Gly  Lys Leu Ala Leu Trp  Gly Glu His
    1910             1915              1920

Thr Gly  Gln Leu Tyr Ser Lys  Phe Leu Leu Lys Ala  Glu Pro Leu
    1925             1930              1935

Ala Phe  Thr Phe Ser His Asp  Tyr Lys Gly Ser Thr  Ser His His
    1940             1945              1950

Leu Val  Ser Arg Lys Ser Ile  Ser Ala Ala Leu Glu  His Lys Val
    1955             1960              1965

Ser Ala  Leu Leu Thr Pro Ala  Glu Gln Thr Gly Thr  Trp Lys Leu
    1970             1975              1980

Lys Thr  Gln Phe Asn Asn Glu  Tyr Ser Gln Asp Leu  Asp Ala
    1985             1990              1995

Tyr Asn  Thr Lys Asp Lys Ile  Gly Val Glu Leu Thr  Gly Arg Thr
    2000             2005              2010

Leu Ala  Asp Leu Thr Leu Leu  Asp Ser Pro Ile Lys  Val Pro Leu
```

-continued

|   |   |   |   |   | 2015 |   |   |   |   | 2020 |   |   |   |   | 2025 |
|---|---|---|---|---|---|---|---|---|---|---|---|---|---|---|---|

Leu Leu Ser Glu Pro Ile Asn Ile Ile Asp Ala Leu Glu Met Arg
        2030                2035                2040

Asp Ala Val Glu Lys Pro Gln Glu Phe Thr Ile Val Ala Phe Val
        2045                2050                2055

Lys Tyr Asp Lys Asn Gln Asp Val His Ser Ile Asn Leu Pro Phe
        2060                2065                2070

Phe Glu Thr Leu Gln Glu Tyr Phe Glu Arg Asn Arg Gln Thr Ile
        2075                2080                2085

Ile Val Val Val Glu Asn Val Gln Arg Asn Leu Lys His Ile Asn
        2090                2095                2100

Ile Asp Gln Phe Val Arg Lys Tyr Arg Ala Ala Leu Gly Lys Leu
        2105                2110                2115

Pro Gln Gln Ala Asn Asp Tyr Leu Asn Ser Phe Asn Trp Glu Arg
        2120                2125                2130

Gln Val Ser His Ala Lys Glu Lys Leu Thr Ala Leu Thr Lys Lys
        2135                2140                2145

Tyr Arg Ile Thr Glu Asn Asp Ile Gln Ile Ala Leu Asp Asp Ala
        2150                2155                2160

Lys Ile Asn Phe Asn Glu Lys Leu Ser Gln Leu Gln Thr Tyr Met
        2165                2170                2175

Ile Gln Phe Asp Gln Tyr Ile Lys Asp Ser Tyr Asp Leu His Asp
        2180                2185                2190

Leu Lys Ile Ala Ile Ala Asn Ile Ile Asp Glu Ile Ile Glu Lys
        2195                2200                2205

Leu Lys Ser Leu Asp Glu His Tyr His Ile Arg Val Asn Leu Val
        2210                2215                2220

Lys Thr Ile His Asp Leu His Leu Phe Ile Glu Asn Ile Asp Phe
        2225                2230                2235

Asn Lys Ser Gly Ser Ser Thr Ala Ser Trp Ile Gln Asn Val Asp
        2240                2245                2250

Thr Lys Tyr Gln Ile Arg Ile Gln Ile Gln Glu Lys Leu Gln Gln
        2255                2260                2265

Leu Lys Arg His Ile Gln Asn Ile Asp Ile Gln His Leu Ala Gly
        2270                2275                2280

Lys Leu Lys Gln His Ile Glu Ala Ile Asp Val Arg Val Leu Leu
        2285                2290                2295

Asp Gln Leu Gly Thr Thr Ile Ser Phe Glu Arg Ile Asn Asp Val
        2300                2305                2310

Leu Glu His Val Lys His Phe Val Ile Asn Leu Ile Gly Asp Phe
        2315                2320                2325

Glu Val Ala Glu Lys Ile Asn Ala Phe Arg Ala Lys Val His Glu
        2330                2335                2340

Leu Ile Glu Arg Tyr Glu Val Asp Gln Gln Ile Gln Val Leu Met
        2345                2350                2355

Asp Lys Leu Val Glu Leu Thr His Gln Tyr Lys Leu Lys Glu Thr
        2360                2365                2370

Ile Gln Lys Leu Ser Asn Val Leu Gln Gln Val Lys Ile Lys Asp
        2375                2380                2385

Tyr Phe Glu Lys Leu Val Gly Phe Ile Asp Asp Ala Val Lys Lys
        2390                2395                2400

Leu Asn Glu Leu Ser Phe Lys Thr Phe Ile Glu Asp Val Asn Lys
        2405                2410                2415

-continued

```
Phe Leu Asp Met Leu Ile Lys Lys Leu Lys Ser Phe Asp Tyr His
    2420                2425                2430

Gln Phe Val Asp Glu Thr Asn Asp Lys Ile Arg Glu Val Thr Gln
    2435                2440                2445

Arg Leu Asn Gly Glu Ile Gln Ala Leu Glu Leu Pro Gln Lys Ala
    2450                2455                2460

Glu Ala Leu Lys Leu Phe Leu Glu Glu Thr Lys Ala Thr Val Ala
    2465                2470                2475

Val Tyr Leu Glu Ser Leu Gln Asp Thr Lys Ile Thr Leu Ile Ile
    2480                2485                2490

Asn Trp Leu Gln Glu Ala Leu Ser Ser Ala Ser Leu Ala His Met
    2495                2500                2505

Lys Ala Lys Phe Arg Glu Thr Leu Glu Asp Thr Arg Asp Arg Met
    2510                2515                2520

Tyr Gln Met Asp Ile Gln Gln Glu Leu Gln Arg Tyr Leu Ser Leu
    2525                2530                2535

Val Gly Gln Val Tyr Ser Thr Leu Val Thr Tyr Ile Ser Asp Trp
    2540                2545                2550

Trp Thr Leu Ala Ala Lys Asn Leu Thr Asp Phe Ala Glu Gln Tyr
    2555                2560                2565

Ser Ile Gln Asp Trp Ala Lys Arg Met Lys Ala Leu Val Glu Gln
    2570                2575                2580

Gly Phe Thr Val Pro Glu Ile Lys Thr Ile Leu Gly Thr Met Pro
    2585                2590                2595

Ala Phe Glu Val Ser Leu Gln Ala Leu Gln Lys Ala Thr Phe Gln
    2600                2605                2610

Thr Pro Asp Phe Ile Val Pro Leu Thr Asp Leu Arg Ile Pro Ser
    2615                2620                2625

Val Gln Ile Asn Phe Lys Asp Leu Lys Asn Ile Lys Ile Pro Ser
    2630                2635                2640

Arg Phe Ser Thr Pro Glu Phe Thr Ile Leu Asn Thr Phe His Ile
    2645                2650                2655

Pro Ser Phe Thr Ile Asp Phe Val Glu Met Lys Val Lys Ile Ile
    2660                2665                2670

Arg Thr Ile Asp Gln Met Gln Asn Ser Glu Leu Gln Trp Pro Val
    2675                2680                2685

Pro Asp Ile Tyr Leu Arg Asp Leu Lys Val Glu Asp Ile Pro Leu
    2690                2695                2700

Ala Arg Ile Thr Leu Pro Asp Phe Arg Leu Pro Glu Ile Ala Ile
    2705                2710                2715

Pro Glu Phe Ile Ile Pro Thr Leu Asn Leu Asn Asp Phe Gln Val
    2720                2725                2730

Pro Asp Leu His Ile Pro Glu Phe Gln Leu Pro His Ile Ser His
    2735                2740                2745

Thr Ile Glu Val Pro Thr Phe Gly Lys Leu Tyr Ser Ile Leu Lys
    2750                2755                2760

Ile Gln Ser Pro Leu Phe Thr Leu Asp Ala Asn Ala Asp Ile Gly
    2765                2770                2775

Asn Gly Thr Thr Ser Ala Asn Glu Ala Gly Ile Ala Ala Ser Ile
    2780                2785                2790

Thr Ala Lys Gly Glu Ser Lys Leu Glu Val Leu Asn Phe Asp Phe
    2795                2800                2805
```

-continued

```
Gln Ala Asn Ala Gln Leu Ser Asn Pro Lys Ile Asn Pro Leu Ala
2810                2815                2820

Leu Lys Glu Ser Val Lys Phe Ser Ser Lys Tyr Leu Arg Thr Glu
2825                2830                2835

His Gly Ser Glu Met Leu Phe Phe Gly Asn Ala Ile Glu Gly Lys
2840                2845                2850

Ser Asn Thr Val Ala Ser Leu His Thr Glu Lys Asn Thr Leu Glu
2855                2860                2865

Leu Ser Asn Gly Val Ile Val Lys Ile Asn Asn Gln Leu Thr Leu
2870                2875                2880

Asp Ser Asn Thr Lys Tyr Phe His Lys Leu Asn Ile Pro Lys Leu
2885                2890                2895

Asp Phe Ser Ser Gln Ala Asp Leu Arg Asn Glu Ile Lys Thr Leu
2900                2905                2910

Leu Lys Ala Gly His Ile Ala Trp Thr Ser Ser Gly Lys Gly Ser
2915                2920                2925

Trp Lys Trp Ala Cys Pro Arg Phe Ser Asp Glu Gly Thr His Glu
2930                2935                2940

Ser Gln Ile Ser Phe Thr Ile Glu Gly Pro Leu Thr Ser Phe Gly
2945                2950                2955

Leu Ser Asn Lys Ile Asn Ser Lys His Leu Arg Val Asn Gln Asn
2960                2965                2970

Leu Val Tyr Glu Ser Gly Ser Leu Asn Phe Ser Lys Leu Glu Ile
2975                2980                2985

Gln Ser Gln Val Asp Ser Gln His Val Gly His Ser Val Leu Thr
2990                2995                3000

Ala Lys Gly Met Ala Leu Phe Gly Glu Gly Lys Ala Glu Phe Thr
3005                3010                3015

Gly Arg His Asp Ala His Leu Asn Gly Lys Val Ile Gly Thr Leu
3020                3025                3030

Lys Asn Ser Leu Phe Phe Ser Ala Gln Pro Phe Glu Ile Thr Ala
3035                3040                3045

Ser Thr Asn Asn Glu Gly Asn Leu Lys Val Arg Phe Pro Leu Arg
3050                3055                3060

Leu Thr Gly Lys Ile Asp Phe Leu Asn Asn Tyr Ala Leu Phe Leu
3065                3070                3075

Ser Pro Ser Ala Gln Gln Ala Ser Trp Gln Val Ser Ala Arg Phe
3080                3085                3090

Asn Gln Tyr Lys Tyr Asn Gln Asn Phe Ser Ala Gly Asn Asn Glu
3095                3100                3105

Asn Ile Met Glu Ala His Val Gly Ile Asn Gly Glu Ala Asn Leu
3110                3115                3120

Asp Phe Leu Asn Ile Pro Leu Thr Ile Pro Glu Met Arg Leu Pro
3125                3130                3135

Tyr Thr Ile Ile Thr Thr Pro Pro Leu Lys Asp Phe Ser Leu Trp
3140                3145                3150

Glu Lys Thr Gly Leu Lys Glu Phe Leu Lys Thr Thr Lys Gln Ser
3155                3160                3165

Phe Asp Leu Ser Val Lys Ala Gln Tyr Lys Lys Asn Lys His Arg
3170                3175                3180

His Ser Ile Thr Asn Pro Leu Ala Val Leu Cys Glu Phe Ile Ser
3185                3190                3195

Gln Ser Ile Lys Ser Phe Asp Arg His Phe Glu Lys Asn Arg Asn
```

-continued

```
            3200              3205              3210
Asn Ala Leu Asp Phe Val Thr Lys Ser Tyr Asn Glu Thr Lys Ile
            3215              3220              3225
Lys Phe Asp Lys Tyr Lys Ala Glu Lys Ser His Asp Glu Leu Pro
            3230              3235              3240
Arg Thr Phe Gln Ile Pro Gly Tyr Thr Val Pro Val Val Asn Val
            3245              3250              3255
Glu Val Ser Pro Phe Thr Ile Glu Met Ser Ala Phe Gly Tyr Val
            3260              3265              3270
Phe Pro Lys Ala Val Ser Met Pro Ser Phe Ser Ile Leu Gly Ser
            3275              3280              3285
Asp Val Arg Val Pro Ser Tyr Thr Leu Ile Leu Pro Ser Leu Glu
            3290              3295              3300
Leu Pro Val Leu His Val Pro Arg Asn Leu Lys Leu Ser Leu Pro
            3305              3310              3315
His Phe Lys Glu Leu Cys Thr Ile Ser His Ile Phe Ile Pro Ala
            3320              3325              3330
Met Gly Asn Ile Thr Tyr Asp Phe Ser Phe Lys Ser Ser Val Ile
            3335              3340              3345
Thr Leu Asn Thr Asn Ala Glu Leu Phe Asn Gln Ser Asp Ile Val
            3350              3355              3360
Ala His Leu Leu Ser Ser Ser Ser Ser Val Ile Asp Ala Leu Gln
            3365              3370              3375
Tyr Lys Leu Glu Gly Thr Thr Arg Leu Thr Arg Lys Arg Gly Leu
            3380              3385              3390
Lys Leu Ala Thr Ala Leu Ser Leu Ser Asn Lys Phe Val Glu Gly
            3395              3400              3405
Ser His Asn Ser Thr Val Ser Leu Thr Thr Lys Asn Met Glu Val
            3410              3415              3420
Ser Val Ala Lys Thr Thr Lys Ala Glu Ile Pro Ile Leu Arg Met
            3425              3430              3435
Asn Phe Lys Gln Glu Leu Asn Gly Asn Thr Lys Ser Lys Pro Thr
            3440              3445              3450
Val Ser Ser Ser Met Glu Phe Lys Tyr Asp Phe Asn Ser Ser Met
            3455              3460              3465
Leu Tyr Ser Thr Ala Lys Gly Ala Val Asp His Lys Leu Ser Leu
            3470              3475              3480
Glu Ser Leu Thr Ser Tyr Phe Ser Ile Glu Ser Ser Thr Lys Gly
            3485              3490              3495
Asp Val Lys Gly Ser Val Leu Ser Arg Glu Tyr Ser Gly Thr Ile
            3500              3505              3510
Ala Ser Glu Ala Asn Thr Tyr Leu Asn Ser Lys Ser Thr Arg Ser
            3515              3520              3525
Ser Val Lys Leu Gln Gly Thr Ser Lys Ile Asp Asp Ile Trp Asn
            3530              3535              3540
Leu Glu Val Lys Glu Asn Phe Ala Gly Glu Ala Thr Leu Gln Arg
            3545              3550              3555
Ile Tyr Ser Leu Trp Glu His Ser Thr Lys Asn His Leu Gln Leu
            3560              3565              3570
Glu Gly Leu Phe Phe Thr Asn Gly Glu His Thr Ser Lys Ala Thr
            3575              3580              3585
Leu Glu Leu Ser Pro Trp Gln Met Ser Ala Leu Val Gln Val His
            3590              3595              3600
```

```
Ala Ser Gln Pro Ser Ser Phe His Asp Phe Pro Asp Leu Gly Gln
    3605            3610            3615

Glu Val Ala Leu Asn Ala Asn Thr Lys Asn Gln Lys Ile Arg Trp
    3620            3625            3630

Lys Asn Glu Val Arg Ile His Ser Gly Ser Phe Gln Ser Gln Val
    3635            3640            3645

Glu Leu Ser Asn Asp Gln Glu Lys Ala His Leu Asp Ile Ala Gly
    3650            3655            3660

Ser Leu Glu Gly His Leu Arg Phe Leu Lys Asn Ile Ile Leu Pro
    3665            3670            3675

Val Tyr Asp Lys Ser Leu Trp Asp Phe Leu Lys Leu Asp Val Thr
    3680            3685            3690

Thr Ser Ile Gly Arg Arg Gln His Leu Arg Val Ser Thr Ala Phe
    3695            3700            3705

Val Tyr Thr Lys Asn Pro Asn Gly Tyr Ser Phe Ser Ile Pro Val
    3710            3715            3720

Lys Val Leu Ala Asp Lys Phe Ile Thr Pro Gly Leu Lys Leu Asn
    3725            3730            3735

Asp Leu Asn Ser Val Leu Val Met Pro Thr Phe His Val Pro Phe
    3740            3745            3750

Thr Asp Leu Gln Val Pro Ser Cys Lys Leu Asp Phe Arg Glu Ile
    3755            3760            3765

Gln Ile Tyr Lys Lys Leu Arg Thr Ser Ser Phe Ala Leu Asn Leu
    3770            3775            3780

Pro Thr Leu Pro Glu Val Lys Phe Pro Glu Val Asp Val Leu Thr
    3785            3790            3795

Lys Tyr Ser Gln Pro Glu Asp Ser Leu Ile Pro Phe Phe Glu Ile
    3800            3805            3810

Thr Val Pro Glu Ser Gln Leu Thr Val Ser Gln Phe Thr Leu Pro
    3815            3820            3825

Lys Ser Val Ser Asp Gly Ile Ala Ala Leu Asp Leu Asn Ala Val
    3830            3835            3840

Ala Asn Lys Ile Ala Asp Phe Glu Leu Pro Thr Ile Ile Val Pro
    3845            3850            3855

Glu Gln Thr Ile Glu Ile Pro Ser Ile Lys Phe Ser Val Pro Ala
    3860            3865            3870

Gly Ile Val Ile Pro Ser Phe Gln Ala Leu Thr Ala Arg Phe Glu
    3875            3880            3885

Val Asp Ser Pro Val Tyr Asn Ala Thr Trp Ser Ala Ser Leu Lys
    3890            3895            3900

Asn Lys Ala Asp Tyr Val Glu Thr Val Leu Asp Ser Thr Cys Ser
    3905            3910            3915

Ser Thr Val Gln Phe Leu Glu Tyr Glu Leu Asn Val Leu Gly Thr
    3920            3925            3930

His Lys Ile Glu Asp Gly Thr Leu Ala Ser Lys Thr Lys Gly Thr
    3935            3940            3945

Leu Ala His Arg Asp Phe Ser Ala Glu Tyr Glu Glu Asp Gly Lys
    3950            3955            3960

Phe Glu Gly Leu Gln Glu Trp Glu Gly Lys Ala His Leu Asn Ile
    3965            3970            3975

Lys Ser Pro Ala Phe Thr Asp Leu His Leu Arg Tyr Gln Lys Asp
    3980            3985            3990
```

-continued

```
Lys Lys Gly Ile Ser Thr Ser Ala Ala Ser Pro Ala Val Gly Thr
    3995            4000              4005

Val Gly Met Asp Met Asp Glu Asp Asp Asp Phe Ser Lys Trp Asn
    4010            4015              4020

Phe Tyr Tyr Ser Pro Gln Ser Ser Pro Asp Lys Lys Leu Thr Ile
    4025            4030              4035

Phe Lys Thr Glu Leu Arg Val Arg Glu Ser Asp Glu Glu Thr Gln
    4040            4045              4050

Ile Lys Val Asn Trp Glu Glu Ala Ala Ser Gly Leu Leu Thr
    4055            4060              4065

Ser Leu Lys Asp Asn Val Pro Lys Ala Thr Gly Val Leu Tyr Asp
    4070            4075              4080

Tyr Val Asn Lys Tyr His Trp Glu His Thr Gly Leu Thr Leu Arg
    4085            4090              4095

Glu Val Ser Ser Lys Leu Arg Arg Asn Leu Gln Asn Asn Ala Glu
    4100            4105              4110

Trp Val Tyr Gln Gly Ala Ile Arg Gln Ile Asp Asp Ile Asp Val
    4115            4120              4125

Arg Phe Gln Lys Ala Ala Ser Gly Thr Thr Gly Thr Tyr Gln Glu
    4130            4135              4140

Trp Lys Asp Lys Ala Gln Asn Leu Tyr Gln Glu Leu Leu Thr Gln
    4145            4150              4155

Glu Gly Gln Ala Ser Phe Gln Gly Leu Lys Asp Asn Val Phe Asp
    4160            4165              4170

Gly Leu Val Arg Val Thr Gln Lys Phe His Met Lys Val Lys His
    4175            4180              4185

Leu Ile Asp Ser Leu Ile Asp Phe Leu Asn Phe Pro Arg Phe Gln
    4190            4195              4200

Phe Pro Gly Lys Pro Gly Ile Tyr Thr Arg Glu Glu Leu Cys Thr
    4205            4210              4215

Met Phe Ile Arg Glu Val Gly Thr Val Leu Ser Gln Val Tyr Ser
    4220            4225              4230

Lys Val His Asn Gly Ser Glu Ile Leu Phe Ser Tyr Phe Gln Asp
    4235            4240              4245

Leu Val Ile Thr Leu Pro Phe Glu Leu Arg Lys His Lys Leu Ile
    4250            4255              4260

Asp Val Ile Ser Met Tyr Arg Glu Leu Leu Lys Asp Leu Ser Lys
    4265            4270              4275

Glu Ala Gln Glu Val Phe Lys Ala Ile Gln Ser Leu Lys Thr Thr
    4280            4285              4290

Glu Val Leu Arg Asn Leu Gln Asp Leu Leu Gln Phe Ile Phe Gln
    4295            4300              4305

Leu Ile Glu Asp Asn Ile Lys Gln Leu Lys Glu Met Lys Phe Thr
    4310            4315              4320

Tyr Leu Ile Asn Tyr Ile Gln Asp Glu Ile Asn Thr Ile Phe Asn
    4325            4330              4335

Asp Tyr Ile Pro Tyr Val Phe Lys Leu Leu Lys Glu Asn Leu Cys
    4340            4345              4350

Leu Asn Leu His Lys Phe Asn Glu Phe Ile Gln Asn Glu Leu Gln
    4355            4360              4365

Glu Ala Ser Gln Glu Leu Gln Gln Ile His Gln Tyr Ile Met Ala
    4370            4375              4380

Leu Arg Glu Glu Tyr Phe Asp Pro Ser Ile Val Gly Trp Thr Val
```

-continued

```
                4385                4390                4395
Lys Tyr Tyr Glu Leu Glu Glu Lys Ile Val Ser Leu Ile Lys Asn
                4400                4405                4410

Leu Leu Val Ala Leu Lys Asp Phe His Ser Glu Tyr Ile Val Ser
        4415                4420                4425

Ala Ser Asn Phe Thr Ser Gln Leu Ser Ser Gln Val Glu Gln Phe
        4430                4435                4440

Leu His Arg Asn Ile Gln Glu Tyr Leu Ser Ile Leu Thr Asp Pro
        4445                4450                4455

Asp Gly Lys Gly Lys Glu Lys Ile Ala Glu Leu Ser Ala Thr Ala
        4460                4465                4470

Gln Glu Ile Ile Lys Ser Gln Ala Ile Ala Thr Lys Lys Ile Ile
        4475                4480                4485

Ser Asp Tyr His Gln Gln Phe Arg Tyr Lys Leu Gln Asp Phe Ser
        4490                4495                4500

Asp Gln Leu Ser Asp Tyr Tyr Glu Lys Phe Ile Ala Glu Ser Lys
        4505                4510                4515

Arg Leu Ile Asp Leu Ser Ile Gln Asn Tyr His Thr Phe Leu Ile
        4520                4525                4530

Tyr Ile Thr Glu Leu Leu Lys Lys Leu Gln Ser Thr Thr Val Met
        4535                4540                4545

Asn Pro Tyr Met Lys Leu Ala Pro Gly Glu Leu Thr Ile Ile Leu
        4550                4555                4560
```

<210> SEQ ID NO 2
<211> LENGTH: 317
<212> TYPE: PRT
<213> ORGANISM: Homo sapiens

<400> SEQUENCE: 2

```
Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
                20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
                100                 105                 110

Lys Glu Leu Gln Ala Ala Gln Ala Arg Leu Gly Ala Asp Met Glu Asp
            115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
                180                 185                 190
```

-continued

```
Ser Ala Ile Arg Glu Arg Leu Gly Pro Leu Val Glu Gln Gly Arg Val
    195                 200                 205
Arg Ala Ala Thr Val Gly Ser Leu Ala Gly Gln Pro Leu Gln Glu Arg
    210                 215                 220
Ala Gln Ala Trp Gly Glu Arg Leu Arg Ala Arg Met Glu Glu Met Gly
225                 230                 235                 240
Ser Arg Thr Arg Asp Arg Leu Asp Glu Val Lys Glu Gln Val Ala Glu
                245                 250                 255
Val Arg Ala Lys Leu Glu Glu Gln Ala Gln Gln Ile Arg Leu Gln Ala
            260                 265                 270
Glu Ala Phe Gln Ala Arg Leu Lys Ser Trp Phe Glu Pro Leu Val Glu
        275                 280                 285
Asp Met Gln Arg Gln Trp Ala Gly Leu Val Glu Lys Val Gln Ala Ala
    290                 295                 300
Val Gly Thr Ser Ala Ala Pro Val Pro Ser Asp Asn His
305                 310                 315

<210> SEQ ID NO 3
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 3

Glu Asn Phe Ala Gly Glu Ala Thr Leu Gln Arg
1               5                   10

<210> SEQ ID NO 4
<211> LENGTH: 22
<212> TYPE: DNA
<213> ORGANISM: Artificial Sequence
<220> FEATURE:
<223> OTHER INFORMATION: Synthetic DNA

<400> SEQUENCE: 4
tcaattgaaa gagctacagg tg                                          22

<210> SEQ ID NO 5
<211> LENGTH: 22
<212> TYPE: DNA
<213> ORGANISM: Artificial Sequence
<220> FEATURE:
<223> OTHER INFORMATION: Synthetic DNA

<400> SEQUENCE: 5
accagtccaa tttaggagag cc                                          22

<210> SEQ ID NO 6
<211> LENGTH: 20
<212> TYPE: DNA
<213> ORGANISM: Artificial Sequence
<220> FEATURE:
<223> OTHER INFORMATION: Synthetic DNA

<400> SEQUENCE: 6
agaccacgag aatgcgaagg                                             20
```

USE OF PRION CONVERSION MODULATING AGENTS

FIELD OF THE INVENTION

This invention relates to the use of apolipoprotein B or apolipoprotein E or fragments or mimetics thereof for diagnostic, detection, prognostic and identifying modulators of the prion protein replication. More specifically, the invention provides the use of modulators of apolipoprotein B or fragments thereof for modulating the prion protein replication which are implicated in the pathogenesis of transmissible spongiform encephalopathies and other prion diseases.

BACKGROUND OF THE INVENTION

Creutzfeldt-Jakob disease (CJD) in humans and scrapie and bovine spongiform encephalopathy (BSE) in animals are some of the diseases that belong to the group of Transmissible Spongiform Encephalopathies (TSE), also known as prion diseases (Prusiner, 1991). These diseases are characterized by an extremely long incubation period, followed by a brief and invariably fatal clinical disease (Roos et al., 1973). To date no therapy is available.

Although these diseases are relatively rare in humans, the risk for the transmissibility of BSE to humans through the food chain has seized the attention of the public health authorities and the scientific community (Soto at al., 2001). Variant CJD (vCJD) is a new disease, which was first described in March 1996 (Will et al., 1996). In contrast to typical cases of sporadic CJD (sCJD), this variant form affects young patients (average age 27 years old) and has a relatively long duration of illness (median 14 months vs. 4.5 months in traditional CJD). A link between vCJD and BSE was first hypothesized because of the association of these two TSEs in place and time (Bruce, 2000). The most recent and powerful evidence comes from studies showing that the transmission characteristics of BSE and vCJD to mice are almost identical and strongly indicating that they are due to the same causative agent (Bruce et al., 1997). Moreover, transgenic mice carrying a human or a bovine gene have now been shown to be susceptible to BSE and vCJD (Scott et al., 1999). Furthermore, no other plausible hypothesis for the occurrence of vCJD has been proposed and intensive CJD surveillance in five European countries, with a low exposure to the BSE agent, has failed to identify any additional cases. In conclusion, the most likely cause of vCJD is exposure to the BSE agent, probably due to dietary contamination with affected bovine central nervous system tissue.

The nature of the transmissible agent has been matter of passionate controversy. Further research, has indicated that the TSE agent differs significantly from viruses and other conventional agents in that it seems not to contain nucleic acids (Prusiner, 1998). Additionally, the physicochemical procedures that inactivate most viruses, such as disrupting nucleic acids, have proved ineffective in decreasing the infectivity of the TSE pathogen. In contrast, the procedures that degrade protein have been found to inactivate the pathogen (Prusiner, 1991). Accordingly, the theory that proposes that the transmissible agent is neither a virus nor other previously known infectious agent, but rather an unconventional agent consisting only of a protein recently gained widespread acceptability (Prusiner, 1998). This new class of pathogen was called a "prion", short for "proteinaceous infectious particle". In TSE, prions are composed mainly of a misfolded protein named $PrP^{Sc}$ (for scrapie PrP), which is a post-translationally modified version of a normal protein, termed $PrP^C$ (Cohen et al., 1998). Chemical differences have not been detected to distinguish these two PrP isoforms and the conversion seems to involve a conformational change whereby the α-helical content of the normal protein diminishes and the amount of β-sheet increases (Pan et al., 1993). The structural changes are followed by alterations in the biochemical properties: $PrP^C$ is soluble in non-denaturing detergents, $PrP^{Sc}$ is insoluble; $PrP^C$ is readily digested by proteases (also called protease sensitive prion protein) while $PrP^{Sc}$ is partially resistant, resulting in the formation of a N-terminally truncated fragment known as PrPres is (protease resistant prion protein) (Cohen et al., 1998).

The notion that endogenous $PrP^C$ is involved in the development of infection is supported by experiments in which endogenous PrP gene was knocked out where the animals were both resistant to prion disease and unable to generate new infectious particles (Bueler et al., 1993). In addition, it is clear that during the tune between the inoculation with the infectious protein and the appearance of the clinical symptoms, there is a dramatic increase in the amount of $PrP^{Sc}$.

These findings suggest that endogenous $PrP^C$ is converted to $PrP^{Sc}$ conformation by the action of an infectious form of the PrP molecule (Soto et al., 2001). Prion replication is hypothesized to occur when $PrP^{Sc}$ in the infecting inoculum interacts specifically with host $PrP^C$, catalyzing its conversion to the pathogenic form of the protein. A physical association between the two isoforms during the infectious process is suggested by the primary sequence specificity in prion transmission (Telling et al., 1994) and by the reported in vitro generation of $PrP^{Sc}$-like molecules by mixing purified $PrP^C$ with $PrP^{Sc}$ (Saborio et al., 2001). However, the exact mechanism underlying the conversion is not known.

Investigations with chimeric transgenes showed that $PrP^{Sc}$ and $PrP^C$ are likely to interact within a central domain delimited by codons 96 and 169 (Prusiner, 1996) and synthetic PrP peptides spanning the region 109-141 proved to be able to bind to $PrP^C$ and compete with $PrP^{Sc}$ interaction (Chabry et al., 1998).

Based on data with transgenic animals, it has been proposed that additional brain factors present in the host are essential for prion propagation (Telling et al., 1995). It has been demonstrated previously that prion conversion does not occur under experimental conditions where purified $PrP^C$ and $PrP^{Sc}$ are mixed and incubated (Saborio et al., 1999) but that the conversion activity is recovered when the bulk of cellular proteins are added back to the sample (Saborio et al., 1999). This finding provides direct evidence that other factors present in the brain are essential to catalyse prion propagation.

The observation that cholesterol depletion decreases the formation of $PrP^{Sc}$ whereas sphingolipid depletion increases $PrP^{Sc}$ formation, suggested that "lipid rafts"(lipid domains in membranes that contain sphingolipids and cholesterol) may be the site of the $PrP^c$ to $PrP^{Sc}$ conversion reaction involving either a raft-associated protein or selected raft lipids (Fantini et al., 2002). However, the role of lipid rafts in prion infectivity is still unclear.

Several in vitro methods of detections of prions in a sample have been developed. The set of known detection methods, include $PrP^{Sc}$ detection methods using specific ligand carriers selected from aminoglycans, fibronectin and Apolipoprotein A (WO 02/065133); methods using the monoclonal antibodies selected from Gö138, 3B5 and 12F10 (Schulz et al., 2000); methods based on the formation of a complex between $PrP^{Sc}$ and Apolipoprotein H (WO 03/005037); or methods based on the $PrP^{Sc}$ in vitro amplification called protein misfolding cyclic amplification (PMCA) described in Saborio et al., 2001 and Lucassen et al., 2003.

Apolipoprotein B is the major protein component of the two known atherogenic lipoproteins, Low Density Lipoproteins (LDL) and remnants of triglyceride-rich lipoproteins. The apolipoprotein B concentration is considered to be a direct reflection of the number of atherogenic particles in the blood and has been proposed as a parameter for determining the risk of atherosclerosis.

Apolipoprotein E is a constituent of several plasma lipoprotein such as chylomicrons, very low-density lipoproteins (VLDL), and high-density lipoproteins (HDL) (Lehninger et al., 1993).

Apolipoprotein E has recently emerged as a major genetic risk factor for Alzheimer's disease, a neurodegenerative disorder (U.S. Pat. No. 6,022,683) and upregulated in the cerebrospinal fluid of patients with variant CJD and Alzheimer's disease compared to patients with sporadic CJD (Choe et al., 2002). The Apolipoprotein E 4/4 phenotype is associated with increased risk of coronary heart diseases and Creutzfeld-Jakob disease (Golaz et al., 1995). Apolipoprotein E gene expression was found to be increased in astrocytes associated with the neuropathological lesions in a scrapie animal model (Dietrich et al., 1991).

Apolipoprotein E was found to recognise a shared structural motif of amyloids and prion which, after induction, can accelerate the adoption of a beta-sheet conformation (Baumann et al., 2000).

Apolipoprotein B and E are ligands for the LDL receptor and are known for its prominent role in cholesterol transport and plasma lipoprotein metabolism via LDL receptor interactions (Segrest et al, 2001; Clavey et al, 1991).

One approach to the treatment and prevention of prion diseases has been to develop agents for blocking the transformation of $PrP^c$ into $PrP^{Sc}$. Some agents proposed were Congo red dye (U.S. Pat. No. 5,276,059), nerve growth peptides (U.S. Pat. No. 5,134,121), fragments of prion proteins (U.S. Pat. No. 6,355,610), compounds that reduces Apolipoprotein E release in the brain tissue (US 2002/0155426), therapeutic agents that prevent Apolipoprotein E4 to interact with neuronal LDL receptor-related protein (WO 97/14437), compounds that increase Apolipoprotein E levels (WO 99/15159) and beta-sheet breaker peptides (U.S. Pat. No. 5,948,763).

It would be desirable to develop new methods for identifying and inhibiting the prion conversion factor(s).

SUMMARY OF THE INVENTION

It is an object of the invention to provide a use of peptides or proteins in an assay for the detection of $PrP^{Sc}$ formation in a sample.

It is also an object of the invention to provide a use of peptides or proteins in a screening assay for identifying compounds that modulate the conversion of $PrP^c$ into $PrP^{Sc}$.

It is further an object of the invention to provide a substance which is suitable for the treatment of, and/or prevention of, and/or delaying the progression of prion related disorders, notably, bovine spongiform encephalopathy (BSE) and Creutzfeld-Jacob Disease (CJD).

In a first aspect, the invention provides a use of a peptide or a protein selected from Apolipoprotein B; a fragment or mimetic thereof; Apolipoprotein E and a fragment or mimetic thereof, in an assay for the detection of $PrP^{Sc}$ formation in a sample.

In a second aspect, the invention provides a use of a peptide or a protein selected from Apolipoprotein B; a fragment or mimetic thereof; Apolipoprotein E and a fragment or mimetic thereof, in a screening assay for identifying compounds that modulate the conversion of $PrP^c$ into $PrP^{Sc}$.

In a third aspect, the invention provides a use of a modulator, preferably an inhibitor or an antagonist, of a peptide or a protein, wherein the peptide or the protein is selected from Apolipoprotein B; a fragment and a mimetic thereof, for the preparation of a pharmaceutical composition for the treatment of a prion disease, notably, bovine spongiform encephalopathy (BSE) and a Creutzfeld-Jacob Disease (CJD).

In a fourth aspect, the invention provides a method for the diagnosis or detection of a prion disease within a subject suspected of suffering from such a disease which comprises (i) contacting a sample from said subject with a peptide or a protein selected from Apolipoprotein B; a fragment or a mimetic thereof; Apolipoprotein E; a fragment thereof and a mimetic thereof; (ii) contacting the sample obtained from step (i) with $PrP^C$ or $PrP^C$ containing mixtures, such as brain homogenates, cell lysates, lipid rafts preparation; and (iii) determining the presence and/or amount of $PrP^{Sc}$ in said sample.

In a fifth aspect, the invention provides a method of determining a marker that predisposes a subject to a prion disease, comprising (i) measuring a level of a protein selected from Apolipoprotein B and a fragment thereof; and (ii) correlating said level of protein obtained in said measuring step with the occurrence of a prion disease.

In a sixth aspect, the invention provides a method for the detection of $PrP^{Sc}$ formation within a sample, which assay comprises (i) contacting said sample with a peptide or a protein selected from Apolipoprotein B; a fragment or a mimetic thereof; Apolipoprotein E; a fragment thereof and a mimetic thereof (ii) contacting the sample obtained from step (i) with $PrP^C$ or $PrP^C$ containing mixtures, such as brain homogenates, cell lysates, lipid rafts preparation; and (iii) determining the presence and/or amount of $PrP^{Sc}$ in said sample.

In a seventh aspect, the invention provides a method for identifying a compound which modulates, preferably inhibits or antagonizes, the transition of $PrP^C$ into $PrP^{Sc}$ comprising: (i) contacting said sample with a peptide or a protein selected from Apolipoprotein B; a fragment or a mimetic thereof; Apolipoprotein E; a fragment thereof and a mimetic thereof (a) in the presence of said compound and (b) in the absence of said compound; (ii) contacting the sample obtained from step (i) a and (i) b with $PrP^C$ or $PrP^C$ containing mixtures, such as brain homogenates, cell lysates, lipid rafts preparation; and (iii) determining the amount of $PrP^{Sc}$ (a) in the presence of said compound and (b) in the absence of said compound.

In a eighth aspect, the invention provides an assay for the detection of $PrP^{Sc}$ formation within a sample, which assay comprises (i) contacting said sample with a peptide or a protein selected from Apolipoprotein B; a fragment or a mimetic thereof; Apolipoprotein E; a fragment thereof and a mimetic thereof (ii) contacting the sample obtained from step (i) with $PrP^C$ or $PrP^C$ containing mixtures, such as brain homogenates, cell lysates, lipid rafts preparation; and (iii) determining the presence and/or amount of $PrP^{Sc}$ in said sample.

In a ninth aspect, the invention provides a screening assay for identifying a compound which modulates, preferably inhibits or antagonizes, the transition of $PrP^C$ into $PrP^{Sc}$ comprising: (i) contacting said sample with a peptide or a protein selected from Apolipoprotein B; a fragment or a mimetic thereof; Apolipoprotein E; a fragment thereof and a mimetic thereof (a) in the presence of said compound and (b) in the absence of said compound; (ii) contacting the sample obtained from step (i) a and (i) b with $PrP^C$ or $PrP^C$ containing mixtures, such as brain homogenates, cell lysates, lipid rafts preparation; and (iii) determining the amount of PrP$^{Sc}$ (a) in the presence of said compound and (b) in the absence of said compound.

DETAILED DESCRIPTION OF THE INVENTION

The following paragraphs provide definitions of various terms, and are intended to apply uniformly throughout the specification and claims unless an otherwise expressly set out definition provides a different definition.

The term "Gerstmann-Strassler-Scheinker Disease" abbreviated as "GSS" refers to a form of inherited human prion disease. The disease occurs from an autosomal dominant disorder. Family members who inherit the mutant gene succumb to GSS.

The term "prion" shall mean a transmissible particle known to cause a group of such transmissible conformational diseases (spongiform encephalopathies) in humans and animals. The term "prion" is a contraction of the words "protein" and "infection" and the particles are comprised largely if not exclusively of $PrP^{Sc}$ molecules.

"Prions" are distinct from bacteria, viruses and viroids. Known prions include those which infect animals to cause scrapie, a transmissible, degenerative disease of the nervous system of sheep and goats as well as bovine spongiform encephalopathies (BSE) or mad cow disease and feline spongiform encephalopathies of cats. Four prion diseases known to affect humans are Kuru, Creutzfeldt-Jakob Disease (CJD), Gerstmann-Strassler-Scheinker Disease (GSS), and fatal fimilial insomnia (FFI) (Prusinier, 1991). As used herein prion includes all forms of prions causing all or any of these diseases or others in any animals used—and in particular in humans and in domestic farm animals.

The term "lipid rafts" refers to small platforms, composed of sphingolipids and cholesterol in the outer exoplasmic layer, connected to Cholesterol in the inner cytoplasmic layer of the bilayer that have been reviewed recently (Simons et al., 2000). Lipid rafts can be isolated as they are insoluble in certain detergents such as triton X-100 at 4° C. Therefore, rafts can be purified as detergent-insoluble membranes (DIMs) or detergent-resistant membranes (DRMs) by ultracentrifugation on sucrose gradients. Rafts are enriched in GPI-anchored proteins, as well as proteins involved in signal transduction and intracellular trafficking. In neurons, lipid rafts act as platforms for the signal transduction initiated by several classes of neurotrophic factors (Tsui-Pierchala et al., 2002). Example for lipid rafts extraction is given in Example n°2 §c.

The term "prion conversion factor"refers to a factor comprising proteins, lipids, enzymes or receptors that acts as a co-factor or auxiliary factor involved in the process of conversion of $PrP^C$ into $PrP^{Sc}$ and favors the onset and/or progression of the prion disease.

The terms "standardized prion preparation", "prion preparation" and the like are used interchangeably herein to describe a composition containing prions which composition is obtained for example from brain tissue of mammals substantially the same genetic material as relates to PrP proteins, e.g. brain tissue from a set of mammals which exhibit signs or prion disease or for example a composition which is obtained from chronically prion infected cells.

The terms "sensitive to infection", "sensitive to prion infection" and the like are use for a material from a mammal, including cells, that can be infected with an amount and type of prion which would be expected to cause prion disease or symptoms.

By analogy, the terms "resistant to infection", "resistant to prion infection" and the like are used for a material from a mammal, including cells which has the characteristic to be resistant when infected with an amount and type of prion which would be expected to cause prion disease or symptoms and remain uninfected even after several infective prion material inoculations.

The term "sample" refers to a biological extract from a mammal, including cell sample, body fluid, genetic material such as brain homogenate, cells, lipid rafts or purified peptides and proteins.

The term "incubation time" shall mean the time from inoculation of an animal with a prion until the time when the animal first develops detectable symptoms of disease resulting from infection, it also means the time from inoculation of material from a mammal, e.g. brain homogenate, cells, lipid rafts from cells, with prion until the time when the prion infection is detectable such as through the conversion of $PrP^C$ into $PrP^{Sc}$. Several methods of detection of prion infection and PrP conversion are known by a person skilled in the art.

The terms "fraction" or "fragment" refer to any fragment of the polypeptidic chain of the compound itself, alone or in combination with related molecules or residues bound to it, for example residues of sugars or phosphates, or aggregates of the original polypeptide or peptide. Such molecules can result also from other modifications which do not normally alter primary sequence, for example in vivo or in vitro chemical derivatization of peptides (acetylation or carboxylation), those made by modifying the pattern of phosphorylation (introduction of phosphotyrosine, phosphoserine, or phosphothreonine residues) or glycosylation (by exposing the peptide to enzymes which affect glycosylation e.g., mammalian glycosylating or deglycosylating enzymes) of a peptide during its synthesis and processing or in further processing steps.

The terms "modulator" or "modulatory compound" refer to molecules that modify the functions and/or properties (such as receptor binding, lipid affinity, enzyme interaction, structural arrangement, synthesis, metabolism) of the natural protein "Modulators" or "modulatory compounds" include "agonists" and antagonists". Modulators" include peptides, proteins or fragments thereof, peptidomimetics, organic compounds and antibodies.

The term "mimetic" refer to molecules that mimic the functions and/or properties (such as receptor binding, lipid affinity, enzyme interaction, structural arrangement, synthesis, metabolism) of a natural protein. These compounds have for example the property to either enhance a property of the natural protein (i.e. to lead to the same activity when the compound is added to the natural protein as obtained with an increase in concentration in the natural protein) or to exhibit the same property as a natural protein (i.e. to lead to the same activity when the compound replaces the natural protein). "Mimetics" include peptides, proteins or fragments thereof, peptidomimetics and organic compounds. Examples of Apolipoprotein E mimetics are described in US 20020128175 and WO 2004043403.

The terms "inhibitor" or "antagonist" refer to molecules that alter partially or impair the functions and/or properties (such as receptor binding, lipid affinity, enzyme interaction, structural arrangement, synthesis, secretion, metabolism) of the natural protein. "Inhibitors" or "antagonists" include peptides, proteins or fragments thereof, peptidomimetics, organic compounds and antibodies. Examples of Apolipoprotein B antibodies are described in Choi et al., 1997 and in Wang et al., 2000. Examples of Apolipoprotein antagonists can be antagonists that alter or impair the role of Apolipoproteins B or E in the cholesterol transport pathway. Examples of compounds that alter Apolipoprotein B secretion or synthesis are described in U.S. Pat. Nos. 6,369,075, 6,197,972, WO 03/002533 and WO 03/045921. Other "modulators" or "antagonists" can be modulators of the LDL receptor, preferably LDL-receptor antagonists such as anti-LDL receptor antibodies. Examples of monoclonal antibodies to the LDL receptor are given in WO 01/68710.

The term "protein misfolding cyclic amplification assay" or "YMCA assay" is an assay that for the diagnosis or detection of conformational diseases which comprises a cyclic amplification system to increase the levels of the pathogenic conformer such as described for example in WO 02/04954.

The term "maker" for a disease refers to a biological parameter or value including a genetic character, inherited protein mutation(s), blood level of a protein or an enzyme that is different from the average value in a heterogeneous population of individuals and whose occurrence correlates with the occurrence of said disease with a statistical significance. A "marker" for a disease or condition is typically defined as a certain cut-off level of a said biological variable. A "marker" provides basis for determining the risk (probability of occurrence) of a disease in a subject.

The term "complex" includes the formation of an entity by the interaction of several molecules, several proteins, several peptides together or with a receptor. These interactions may be reversible and/or transient. These interactions may induce changes in the properties of the interacting molecules, proteins, peptides or receptors.

By "effective amount", it is meant a concentration of peptide(s) that is capable of slowing down or inhibiting the formation of $PrP^{Sc}$ deposits, or of dissolving preformed deposits. Such concentrations can be routinely determined by those of skill in the art. It will also be appreciated by those of skill in the art that the dosage may be dependent on the stability of the administered peptide. A less stable peptide may require administration in multiple doses.

The preparation of antibodies is known by the person skilled in the art. It is referred by "antibody" to a monoclonal antibody, chimeric antibody, humanized antibody, anti-anti-Id antibody or fragment thereof which specifically recognises and binds to Apo B or Apo E and fragments thereof. For example, monoclonal antibodies are obtained though the generation of hybridoma cells lines producing monoclonal antibodies capable of specifically recognising and binding Apo B and/or fragments thereof. More specifically, these monoclonal antibodies are capable of specifically recognising and binding Apo B. A monoclonal antibody can be prepared in a conventional manner, e.g. by growing a cloned hybridoma comprising a spleen cell from a mammal immunized with hApo B and a homogenic or heterogenic lymphoid cell in liquid medium or mammalian abdomen to allow the hybridoma to produce and accumulate the monoclonal antibody. Preferably, the antibody specifically recognises and binds to Apo B-LDL recognizing fragments.

The present invention provides compounds capable of controlling, including increasing and/or inhibiting, the conversion of $PrP^C$ into $PrP^{Sc}$ in prion diseases.

The activity of the compounds of the invention in controlling the conversion of $PrP^C$ into $PrP^{Sc}$ in prion diseases can be detected using, for example, an in vitro assay, such as that described by Saborio et al., 2001 which measures the ability of compounds of the invention to modulate the conversion of $PrP^C$ into $PrP^{Sc}$. Results are reported in the Examples.

In one embodiment, the invention provides a use of a peptide or a protein selected from Apolipoprotein B; a fragment thereof or a mimetic thereof; Apolipoprotein E; a fragment thereof and a mimetic thereof, preferably Apolipoprotein B; a fragment thereof and a mimetic thereof; in an assay for the detection of $PrP^{sc}$ formation in a sample.

In one further embodiment of the invention, the peptide or the protein selected from Apolipoprotein B; a fragment thereof or a mimetic thereof; Apolipoprotein E; a fragment thereof or a mimetic thereof, preferably Apolipoprotein B or a fragment thereof; used in an assay for the detection of $PrP^{Sc}$ formation in a sample binds and/or forms a complex with the LDL receptor.

In another embodiment, the invention provides a use of a peptide or a protein selected from Apolipoprotein B; a fragment thereof or a mimetic thereof; Apolipoprotein E (SEQ ID NO: 2); a fragment thereof and a mimetic thereof, preferably Apolipoprotein B or a fragment thereof, in a screening assay for the identifying compounds that modulate the conversion of $PrP^c$ into $PrP^{Sc}$.

In another further embodiment of the invention, the peptide or the protein selected from Apolipoprotein B; a fragment thereof or a mimetic; Apolipoprotein E; a fragment thereof and a mimetic thereof, preferably Apolipoprotein B or a fragment thereof, thereof, is used in a screening assay for the identifying compounds that modulate the conversion of $PrP^c$ into $PrP^{Sc}$ binds and/or forms a complex with the LDL receptor.

In a further embodiment of the invention, the assay is a Protein Misfolding Cyclic (PMCA) assay.

In a preferred embodiment of the invention, the Protein Misfolding Cyclic (PMCA) assay uses normal brain homogenate as a source of normal $PrP^c$ and prion conversion factor.

In a further embodiment of the invention, the protein according to the invention is Apolipoprotein B.

In a preferred embodiment of the invention, the Protein Misfolding Cyclic (PMCA) assay uses cell lysates or lipid rafts extracted from prion infection sensitive neuroblasma cells, such as line N2a, described in Example 2, and equivalent, as a source of normal $PrP^c$ and prion conversion actor. Lipid raft fractions can also be purified directly from the brain to serve as a source of substrate for PMCA.

In a preferred embodiment, the invention provides a use of Apolipoprotein B in an assays for the detection of $PrP^C$ in a sample, wherein the assay is a Protein Misfolding Cyclic Amplification (PMCA) assay using lipid rafts from infection sensitive neuroblasma cell line N2a as a source of normal $PrP^C$ and substrate.

In another embodiment, the invention provides a use of a modulator, preferably an inhibitor or an antagonist, of a peptide or a protein, wherein the peptide or the protein is selected from Apolipoprotein B; a fragment thereof or a mimetic thereof for the preparation of a pharmaceutical composition for the treatment of a prion disease, notably, bovine spongiform encephalopathy (BSE) and Creutzfeld-Jacob Disease (CJD). The modulator modifies for example the functions and/or properties of Apolipoprotein B or of a fragment thereof.

In a further embodiment of the invention, the modulator, preferably an inhibitor or an antagonist, of a peptide or a protein, wherein the peptide or the protein is selected from Apolipoprotein B; a fragment thereof and a mimetic thereof which modifies, preferably inhibits the binding and/or the formation of a complex between Apolipoprotein B and the LDL receptor. An example of such modulator can be a LDL receptor modulator, such as a LDL-receptor antagonist such as an anti-LDL receptor antibody.

In a preferred embodiment of the invention, the modulator is an antagonist to Apolipoprotein B or a fragment there In a further preferred embodiment of the invention, the modulator is an antibody raised against Apolipoprotein B or against a fragment thereof.

In another preferred embodiment of the invention, the modulator is an antibody raised against Apolipoprotein B.

In another preferred embodiment of the invention, the modulator is an antibody raised against a fragment of Apolipoprotein B, which fragment is of, or about, a molecular weight selected from 30, 35 and 40 kDa.

In another preferred embodiment of the invention, the modulator is an antibody raised against a fragment of Apolipoprotein B (SEQ ID NO: 1), which fragment comprises a sequence selected from fragments taken between positions 3201-3558, 3548-3905, 3201-3905, 3291-3558, 3548-3815, and 3291-3815.

In a preferred embodiment of the invention, the peptide or protein is selected from Apolipoprotein B or a fragment thereof.

In a preferred embodiment of the invention, the peptide or protein contains the sequence of SEQ D NO: 3.

In another preferred embodiment of the invention, the peptide or protein is a fragment which is of, or about, a molecular weight selected from 30, 35 and 40 kDa.

In another preferred embodiment of the invention, the peptide or protein is a fragment of Apolipoprotein B, comprising a sequence selected from fragments, taken between positions 3201-3558, 3548-3905, 3201-3905, 3291-3558, 3548-3815 and 3291-3815.

In an embodiment of the invention, the invention provides a method for the diagnosis or detection of a prion disease within a subject suspected of suffering from such a disease which comprises (i) contacting a sample from said subject with a peptide or a protein selected from Apolipoprotein B; a fragment or a mimetic thereof; Apolipoprotein E; a fragment thereof and a mimetic thereof; preferably Apolipoprotein B or a fragment thereof, (ii) contacting the sample obtained from step (i) with $PrP^C$ or $PrP^C$ containing mixtures, such as brain homogenates, cell lysates, lipid rafts preparation; and (ii) determining the presence and/or amount of $PrP^{Sc}$ in said sample. The sample from the subject includes a biological extract from a mammal such as cell sample, genetic material, body fluid, brain homogenate, cells and lipid rafts.

In another embodiment of the invention, the invention provides a method of determining a marker that predisposes a subject to a prion disease, comprising (i) measuring a level of a protein selected from Apolipoprotein B and a fragment thereof in said sample; (ii) contacting the sample obtained from step (i) with $PrP^C$ or $PrP^C$ containing mixtures, such as brain homogenates, cell lysates, lipid rafts preparation; and (iii) correlating said level of protein obtained in said measuring step with the occurrence of a prion disease. The maker includes a biological parameter or value such as a genetic character, inherited protein mutation(s), blood level of a protein or an enzyme.

In another embodiment of the invention, the invention provides a method for the detection of $PrP^{Sc}$ formation within a sample, which assay comprises (i) contacting said sample with a peptide or a protein selected from Apolipoprotein B; a fragment thereof or a mimetic thereof; Apolipoprotein E, a fragment thereof and a mimetic thereof, preferably Apolipoprotein B or a fragment thereof (ii) contacting the sample obtained from step (i) with $PrP^C$ or $PrP^C$ containing mixtures, such as brain homogenates, cell lysates, lipid rafts preparation; and (iii) determining the presence and/or amount of $PrP^{Sc}$ in said sample. The sample can be a biological preparation for which the presence of prion is to be detected for quality control reasons and/or a sample extracted from a subject that is suspected of suffering of such a disease, including a biological extract from a mammal such as cell sample, genetic material, body fluid, brain homogenate, cells and lipid rafts.

In another embodiment of the invention, the invention provides a method for identifying, in a sample, a compound which modulates, preferably inhibits or antagonizes, the transition of $PrP^C$ into $PrP^{Sc}$ comprising: (i) contacting said sample with a peptide or a protein selected from Apolipoprotein B; a fragment thereof or a mimetic thereof; Apolipoprotein E, a fragment thereof and a mimetic thereof, preferably Apolipoprotein B or a fragment thereof (ii) contacting the sample obtained from step (i) (a) in the presence of said compound and (b) in the absence of said compound; (iii) contacting the sample obtained from step (i) a and (i) b, with $PrP^C$ or $PrP^C$ containing mixtures, such as brain homogenates, cell lysates, lipid rafts preparation; and (iv) determining the amount of $PrP^{Sc}$ (a) in the presence of said compound and (b) in the absence of said compound. The modulator, includes antibodies, inhibitors of Apolipoproteins B binding, including binding to the LDL receptor, and/or secretion and/or synthesis.

Still another embodiment of the present invention, is a method for treating or preventing a prion disease such as bovine spongiform encephalopathy (BSE) and Creutzfeld-Jacob Disease (CJD), wherein the method comprises administering an effective dose of the above-mentioned modulator of a peptide or a protein, wherein the peptide or the protein is selected from Apolipoprotein B and a fragment thereof, to a subject in the need thereof, wherein the subject can be human or animal.

In a preferred method of use of the modulators, preferably inhibitors, administration of the modulators is by injection or infusion, at periodic intervals. The administration of a compound of the invention may begin before any symptoms are detected in the patient, and should continue thereafter.

The above-mentioned modulatory compounds of the present invention may be administered by any means that achieves the intended purpose. For example, administration may be by a number of different routes including, but not limited to subcutaneous, intravenous, intradermal, intramuscular, intraperitoneal, intra-cerebral, intrathecal, intranasal, oral, rectal, transdermal, intranasal or buccal. Preferably the compounds of the invention are administered by subcutaneous, intramuscular or intravenous injection or infusion.

Parenteral administration can be by bolus injection or by gradual perfusion over time. A typical regimen for preventing, suppressing, or treating prion related disorders, comprises either (1) administration of an effective amount in one or two doses of a high concentration of modulatory in the range of 0.5 to 10 mg of peptide, more preferably 0.5 to 10 mg of peptide, or (2) administration of an effective amount of the peptide in multiple doses of lower concentrations of modulatory compounds in the range of 10-1000 µg, more preferably 50-500 µg over a period of time up to and including several months to several years. It is understood that the dosage administered will be dependent upon the age, sex, health, and weight of the recipient, concurrent treatment, if any, frequency of treatment, and the nature of the effect desired. The total dose required for each treatment may be administered by multiple doses or in a single dose.

Preparations for parenteral administration include sterile aqueous or non-aqueous solutions, suspensions, and emulsions, which may contain auxiliary agents or excipients which are known in the art. Suitable formulations for parenteral administration include aqueous solutions of the active compounds in water-soluble form, for example, water-soluble salts. In addition, suspension of the active compound as appropriate oily injections suspensions may be administered.

In another embodiment of the invention is provided an assay for the detection of the formation of $PrP^{Sc}$ within a sample, which assay comprises (i) contacting said sample with a peptide or a protein selected from Apolipoprotein B; a fragment thereof or a mimetic thereof; Apolipoprotein E, a fragment thereof and a mimetic thereof, preferably Apolipoprotein B or a fragment thereof (iii) contacting the sample obtained from step (iii) contacting the sample obtained from step (ii) with $PrP^C$ or $PrP^C$ containing mixtures, such as brain homogenates, cell lysates, lipid rafts preparation; and (iv) determining the presence and/or amount of $PrP^{Sc}$ in said sample. The sample can be a biological preparation for which the presence of prion is to be detected for quality control reasons and/or a sample extracted from a subject that is suspected of suffering of such a disease, including a biological extract from a mammal such as cell sample, genetic material, body fluid, including blood, serum, plasma, brain homogenate, cells and lipid rafts.

In another embodiment of the invention, is provided a screening assay for identifying a compound which modulates, preferably inhibits or antagonizes, the transition of $PrP^C$ into $PrP^{Sc}$ comprising: (i) contacting said sample with a peptide or a protein selected from Apolipoprotein B; a fragment thereof or a mimetic thereof; Apolipoprotein E; a fragment thereof or a mimetic thereof, preferably Apolipoprotein B or a fragment thereof (a) in the presence of said compound and (b) in the absence of said modulatory compound; (ii) contacting the sample obtained from step (i) a and (i) b with $PrP^C$ or $PrP^C$ containing mixtures, such as brain homogenates, cell lysates, lipid rafts preparation; and (iii) determining the amount of $PrP^{Sc}$ (a) in the presence of said compound and (b) in the absence of said modulatory compound. The modulator, includes antibodies, inhibitors of Apolipoproteins B and/or secretion and/or synthesis.

In further embodiment of the invention, is provided a diagnostic kit for use in the assay of the invention, comprising a probe for receiving a sample and a peptide or a protein selected from Apolipoprotein B; a fragment thereof and a mimetic thereof; Apolipoprotein E, a fragment thereof and a mimetic thereof. The kit of the invention comprises kits having multi-well microtitre plate and/or multi-well sonicator.

In a still further embodiment of the invention, is provided an apparatus for use in the methods of the invention or in the assays of the invention. The apparatus of the invention comprises apparatus that have a microtitre plate and/or multi-well sonicator.

In a preferred embodiment, the prion disease is bovine spongiform encephalopathy (BSE).

In a preferred embodiment, the prion disease is sporadic, variant, familial or iatrogenic Creutzfeld-Jacob Disease (CJD).

The present invention has been described with reference to the specific embodiments, but the content of the description comprises all modifications and substitutions, which can be brought by a person skilled in the art without extending beyond the meaning and purpose of the claims.

The invention will now be described by means of the following Examples, which should not be construed as in any way limiting the present invention. The Examples will refer to the Figures specified here below.

BRIEF DESCRIPTION OF THE DRAWINGS

FIG. 1 shows in vitro prion replication on Hamster brain homogenate by PMCA assay in presence and absence of a cholesterol-depleting agent (Example 1§b). Samples contain 5% normal hamster brain homogenate incubated for 30 min at 4° C. with 0, 5, 10 or 20 mM (final concentration) of methyl-β-cyclodextrin (MβCD). Aliquots of scrapie brain homogenate are added to reach a 3200- (top panel) and 12800-fold (bottom panel) dilution. Half of the samples are frozen immediately as a control without amplification (PMCA "−") and the other half are subjected to 10 cycles of PMCA (PMCA "+"). Prion replication is evaluated by Western Blot after treatment of the samples with PK (100 μg/ml for 60 min). The first lanes in each blot corresponds to the normal brain homogenate not treated with PK.

FIG. 2 shows the effect of Apolipoproteins B, E and J in vitro prion replication on Hamster brain homogenate by PMCA assay Example 1§c). Samples containing 5% normal hamster brain homogenate are incubated with different quantities of human Apolipoprotein B (2A), human Apolipoprotein E (2B) or murine Apolipoprotein J (2C) for 30 min at 4° C. Aliquots of scrapie brain homogenate are added to reach a 3200- (left panel) or 12800-fold (right panel) dilution. Half of the samples are frozen immediately as a control without amplification (PMCA "−") and the other half are subjected to 10 cycles of PMCA (PMCA "+"). Prion replication is evaluated by western blot after treatment of the samples with PK (101 g/ml for 60 min). The first lanes in each blot corresponds to the normal brain homogenate not treated with PK.

FIG. 3 reports differential sensitivity of N2a sub-clones to infection by Scrapie revealed by exposure to anti-$PrP^{Sc}$ 6H4 mabs (Example n°2 §b). Proteinase K (PK) exposure shows were the $PrP^{Sc}$ isoform (Proteinase K resistant) is present. The two sub-clones highlighted #23 and #60 are chosen respectively as representatives of prion infection resistant and sensitive cells. 'N2a' shows uninfected N2a cells processed in parallel. Controls for blotting and PK digestion show 1 μl normal or scrapie brain extract diluted in 80 μl lysis buffer and processed in parallel.

FIG. 4 shows the characterization of PrP in lipid rafts from sub-clones prion infection resistant (#23) and sensitive (#60) N2a (Example 2 §c). FIG. 4A shows PrP quantification by Western blotting in lipid rafts which are extracted from prion infection resistant (#23) and sensitive (#60) cells. The distribution of PrP in the total extract (25 μg loaded) (1), the sucrose sample layer after centrifugation (25 μg loaded) (2) and the bouyant lipid raft fraction (4 μg loaded) (3) are presented. FIG. 4B shows PrP content and glycosylation pattern of the two sub-clones #23 and #60 by Western blotting with anti-PrP. Three independent preparations of lipid rafts prion infection resistant (#23) and sensitive (#60) cells were analysed. Equal amounts (4 μg) of rafts proteins were analysed in each case. FIG. 4C shows the same membrane after stripping and re-probing with anti-actin which confirms the similarity in protein loading.

FIG. 5 presents the in vitro conversion activity of lipid rafts from sub-clones prion infection resistant (#23) and sensitive (#60) N2a using PMCA (Example 2 §d). Upper panel: Lipid rafts are isolated from prion infection resistant (#23) and sensitive (#60) cells. Preparations are mixed in a ratio 100:1 with 10% RML brain homogenate and aliquots are frozen immediately, incubated for 15 h at 37° C. or subjected to 15 cycles of PMCA. Lanes 1: initial mixture without PK digestion; lanes 2: initial mixture digested 10 ug/ml PK 1 hr 37 C; lanes 3: mixture incubated 37° C. PK digested as in lane 2; lanes 4: 15 cycles of PMCA followed by PK digestion as in lane 2. Lane 5 shows the migration and cross-reactivity with anti-PrP of PK alone. Lower panel: Following western blotting the membrane is stained with Coomasie blue to confirm that digestion with PK was complete.

Figure 6:
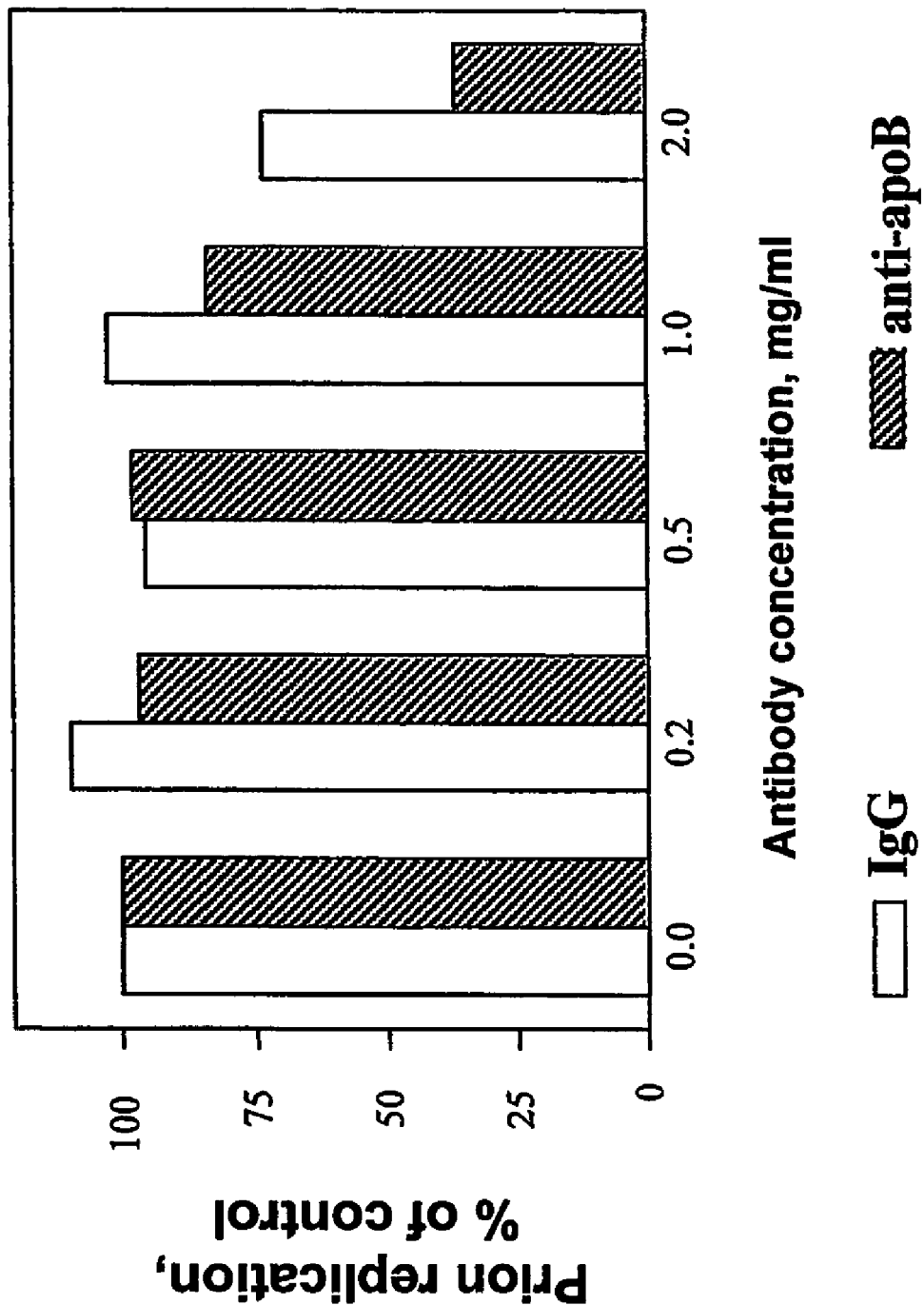

FIG. 6 shows the inhibitory effect on Prion replication in prion infection sensitive cells induced by Anti-hApoB polyclonal antibody (Example 2 §e). Chronically infected #60 sensitive cells were cultured in 24 well culture dishes in the presence of increasing amounts (0-2 mg/ml) of a goat polyclonal antibody against human ApoB (Chemicon) or against a corresponding series of naïve goat IgG. The level of PrP replication was determined by quantitative dot blotting and expressed as chemiluminescent intensity/mg protein. In the graph, for each antibody concentration the chemiluminescent intensity is expressed as a percentage of the value obtained without the antibody. Higher concentrations of anti-hApoB antibody have an inhibitory effect on PrP replication.

Figure 7:
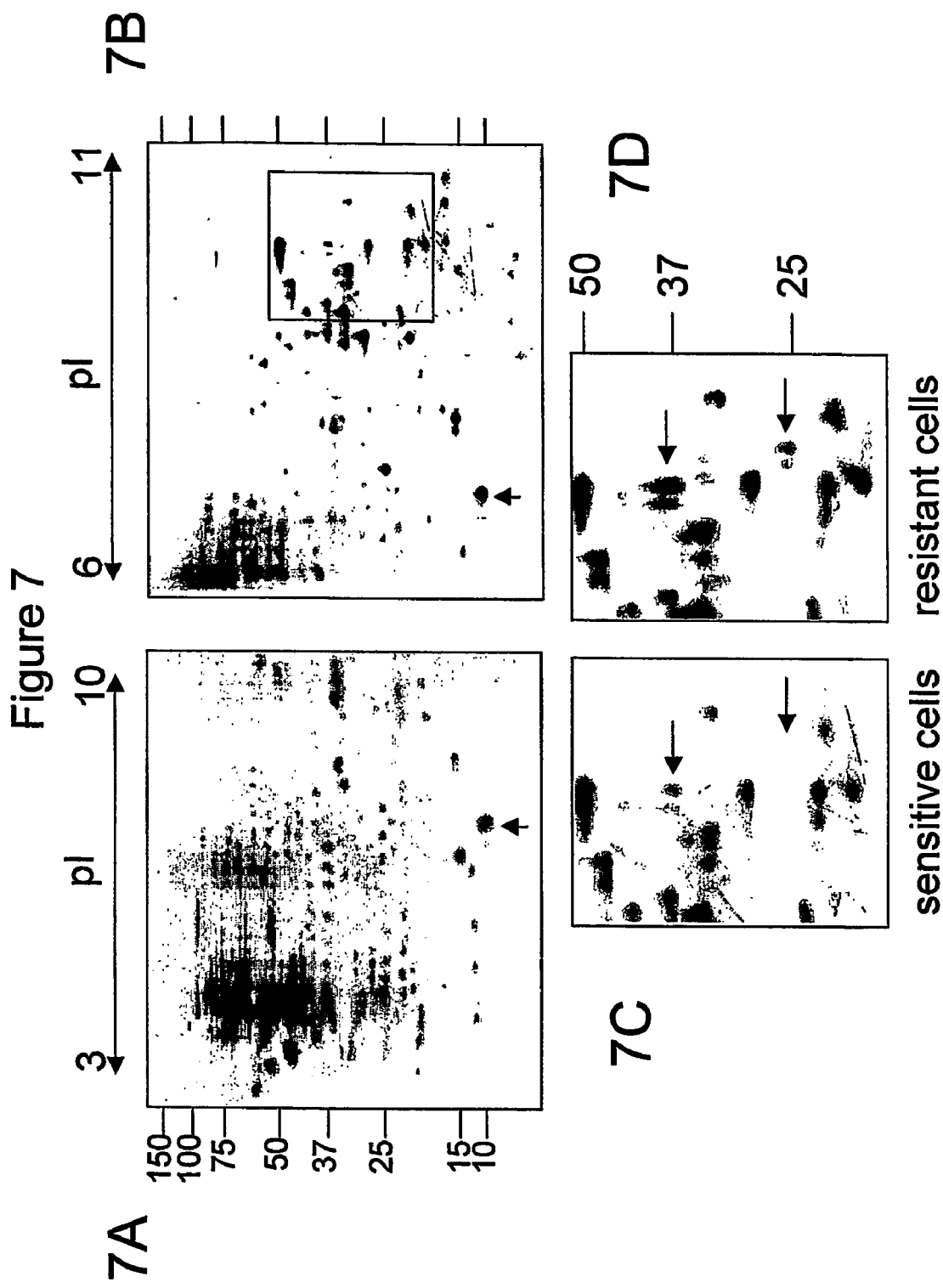

FIG. 7 shows 2D separations of lipid raft proteins from N2a cells (Example 3). Lipid rafts are isolated from prion infection sensitive cells (#60) and 2 aliquots of 25 µg are precipitated with acetone and processed for 2D analysis min the 1st dimension spanning pH ranges 3-10 (7A) or 6-11 (7B). After SDS-PAGE separation in the second dimension, gels are stained using the silver express kit (Invitrogen). Arrow indicates the same protein on both gels (7A and 7B). Proteins within the rectangle shown in B are compared between lipid raft from the prion infection sensitive sub-clone #60, (C) and resistant subclone #23, (D). Arrows indicate proteins which am more abundant in resistant cells.

ABBREVIATIONS

Apo B (Apolipoprotein B; Apo E (apolipoprotein E); Apo J (Apolipoprotein J); BCA (Bicinchoninic Acid); CHAPS (3-((3-cholamidopropyl)dimethylammonio)-1-propane-sulfonate); CNS (central nervous system); BSE (bovine spongiform encephalopathy); CJD (Creutzfeldt-Jakob Disease); DiI (1,1-dioctadecyl-3,3,3,3-tetramethylindocarbocyanine perchlorate); DIM (Detergent-Insoluble Membrane); DMEM (Dulbecco's Modified Eagle Medium); DRM (Detergent-Resistant Membrane); DTT (1,4-Dithio-D,L-threitol); IPG (Immobilized PH Gradient); IEF (Isoelectric Focusing); FCS (Fetal Calf Serum); FFI (Fatal Familial Insomnia); GSS (Gerstmann-Strassler-Scheinker Disease); hr (hour); HRP (Horseradish Peroxidase); kDa (KiloDalton); LDL (Low Density Lipoprotein); µg (microgram); µl (microliter); min (minute); MβCD (methyl-β-cyclodextrin); mM (millimolar); MS (mass spectrometry); PBS (Phosphate Buffered Sulfate); PK (proteinase K); PMCA (Protein Misfolding Cyclic Amplification); PMSF (Phenylmethanesulfonyl Fluoride); PrP (prion protein); $PrP^C$ (normal, non-pathogenic conformer of PrP); $PrP^{Sc}$ (pathogenic or "scrapie" isoform of PrP which is also the marker for prion diseases); PVDF (polyvinylidene difluoride); RPM (Rotation per minute); RML (Rocky Mountain Laboratory); RT-PCR (reverse transcriptase polymerase chain reaction); SDS (Sodium Dodecyl Sulfate); V (Volt); Vol. (volume).

EXAMPLES

The invention will be illustrated by means of the following examples which are not to be construed as limiting the scope of the invention.

The following examples illustrate preferred compounds and methods for determining their biological activities.

PrP scrapie used as infection innoculum is RML (Rocky Mountain Laboratory) strain.

Anti-PrP 6H4 monoclonal antibodies were purchased from Prionics.

Proteinase K was obtained from Boerhinger Ingelheim and Methyl.β.cyclodextrin from Sigma.

Purified and delipidated human Apolipoprotein B (Apo B) and Apolipoprotein E (Apo E) were obtained from Chemicon.

Anti-apo B and anti-apo E are goat polyclonal antibodies against human Apo B and human Apo E, respectively obtained from Chemicon and dialysed against PBS to eliminate sodium azide.

Total goat IgG was purchased from Pierce and dialyzed against PBS.

Mouse neuroblasma N2a cell line was obtained from ATCC.

Murine Apo J (Apo J) was obtained in-house as described in PCT/EP2004/05037.

DiI labeled LDL was obtained from Molecular Probes (L-3482).

Example 1

In vitro Prion Replication in Brain Homogenate Through PMCA Assay

The influence of cholesterol and some of the apolipoproproteins on prion replication in vitro is analysed through a Protein Misfolding Cyclic Amplification assay (PMCA) (Saborio et al., 2001) where hamster brain homogenate is used as a source of $PrP^C$ and conversion factors as follows.

a) Brain Preparation:

Brains from healthy Syrian golden hamsters healthy or infected with the adapted scrapie strain 263 K are obtained after decapitation and immediately frozen in dry ice and kept at –80° until used. Brains are homogenized in PBS containing protease inhibitors (Complete™ cocktail from Boehringer Mannheim) at a 1× final concentration. Detergents (0.5% Triton X-100, 0.05% SDS, final concentrations) are added and samples clarified with low speed centrifugation (10000 g) for 1 min, using an Eppendorf centrifuge (model 5415).

Dilutions (3200-fold and 12800-fold) of the scrapie brain homogenate are added directly to the healthy brain homogenate to trigger prion replication. 60 µl of these mixtures are frozen immediately and another 60 µl are incubated at 37° C. with agitation. Each hour a cycle of sonication (5 pulses of 1 sec each) is done using a microsonicator (Bandelin Electronic, model Sonopuls) with the probe immersed in the sample and the power setting fixed at 40%. These cycles are repeated 10 times.

b) PMCA Signal in Presence and Absence of a Cholesterol-depleting Agent:

Under these conditions a dramatic increase in the amount of $PrP^{Sc}$ signal is observed after 10 cycles of PMCA (FIG. 1, lanes 2 and 3). When normal brain homogenate is treated during 30 min with 10 and 20 mM (but not 5 mM) methyl-β-cyclodextrin (MβCD) a complete inhibition of prion replication is observed (FIG. 1, lanes 6-9) as obtained in mouse models in cell cultures and in vitro, indicating that cholesterol depletion has a detrimental effect on prion replication (Taraboulos et al., 1995).

c) PMCA Signal in Presence of Apolipoproteins

Figure 2A:
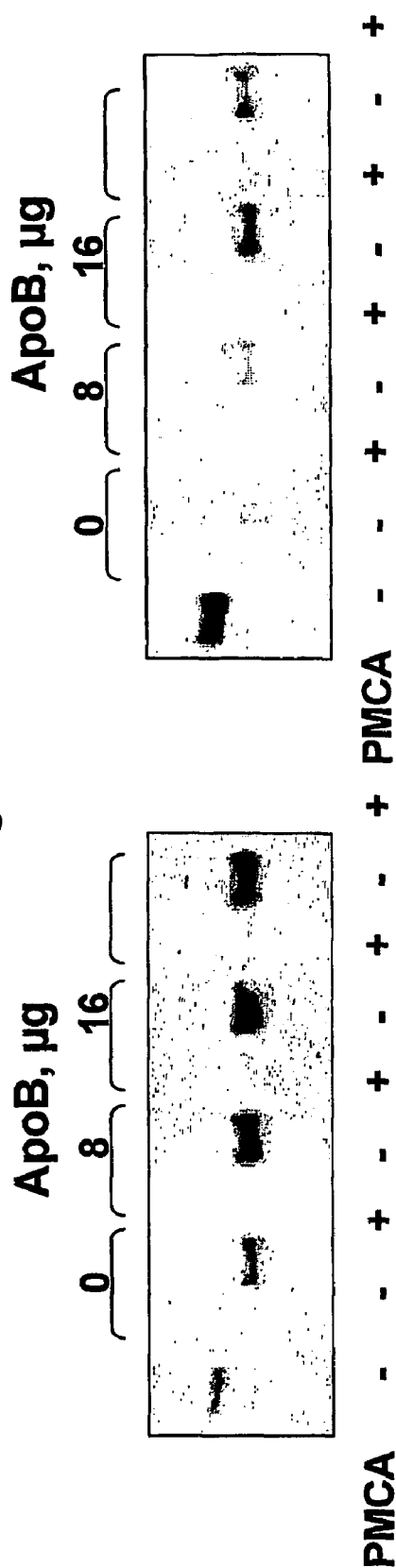
Figure 2B:
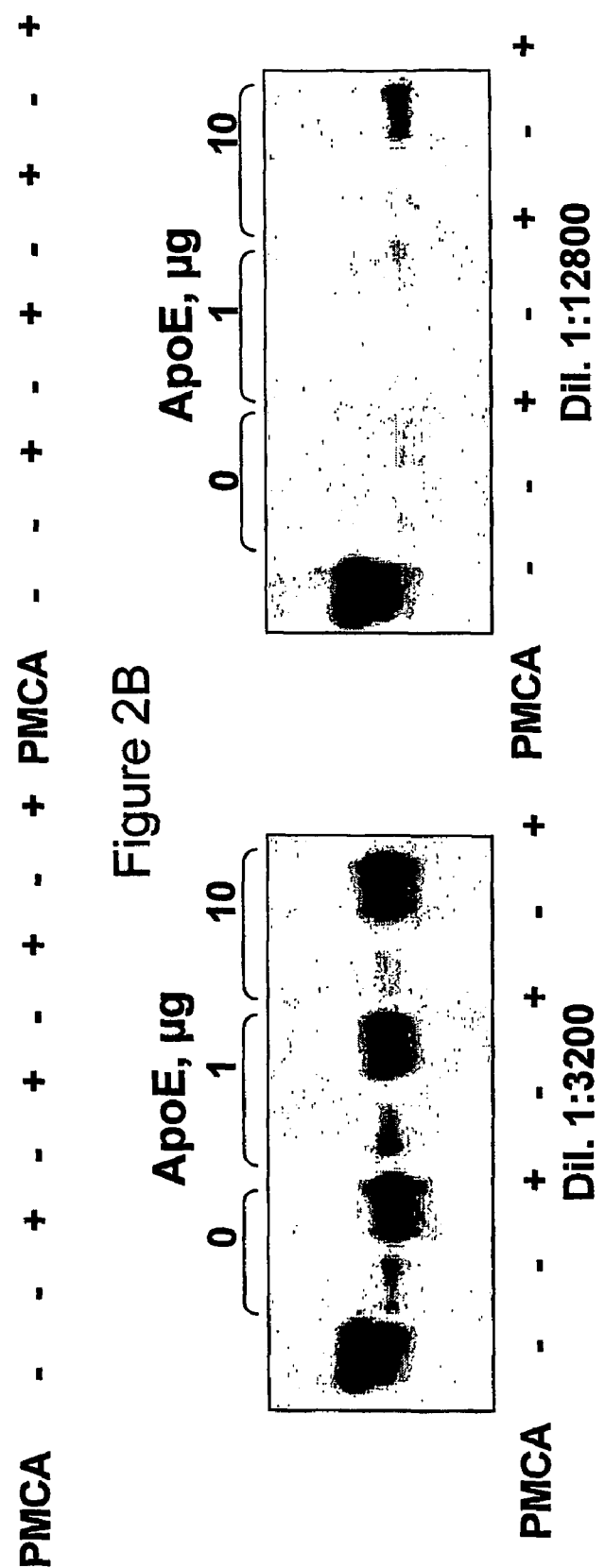
Figure 2C:
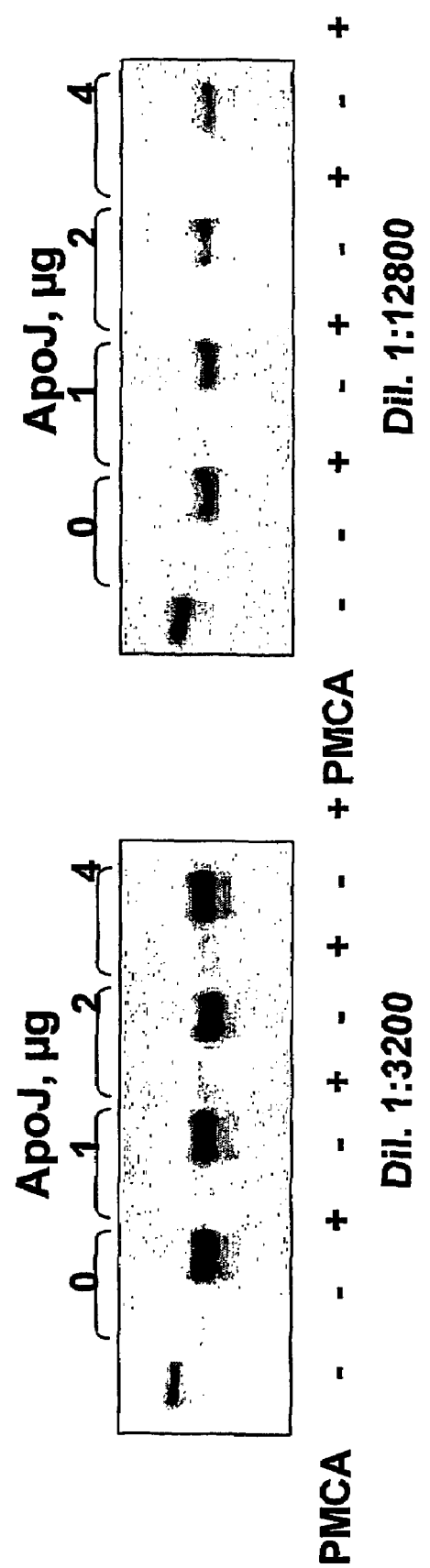
Figure 3:
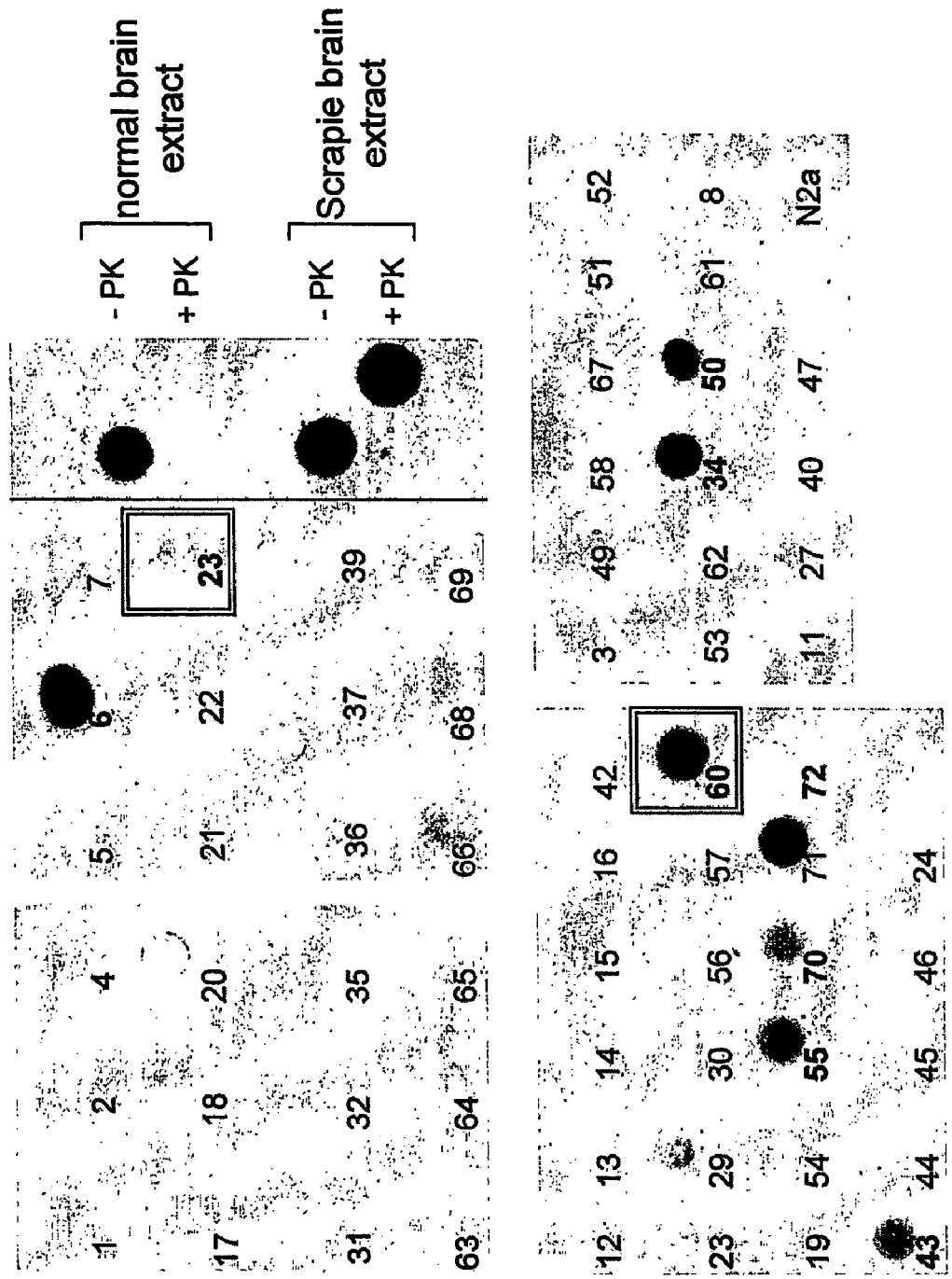

Purified delipidated human ApoB (FIG. 2A) and human Apo E (FIG. 2B) are respectively added to the PMCA preparation without cyclodextrin at different concentrations (8 and 16 μg for hApo B) and (1 and 10 μg for hApo E). Samples are incubated for 30 min at 4° C. and thereafter half of each sample is frozen and the other half subjected to PMCA cycles.

An increase in prion replication in vitro is observed at both 3200-fold and 12800-fold dilutions of scrapie brain homogenate for both Apolipoprotein B and Apolipoprotein E.

In contrast, addition of Apolipoprotein J (at concentrations of 1, 2 and 4 μg), an Apolipoprotein component of HDL, has no effect on PMCA signal (FIG. 2C).

These data show the effect of Apolipoprotein B and E implicated in the prion conversion.

Example 2

In vitro Prion Replication in Lipid Rafts from Prion Infection Sensitive Cells by PMCA The mouse neuroblastoma cell line N2a is used for their capability to be infected with PrPSc. Baron et al., 2002 and Enari et al., 2001 have shown that prion infection sensitive and prion infection resistant N2a sub-lines exist. Lipid rafts from the prion infection sensitive line are isolated and used as a substrate for PMCA assay. The effect of an apolipoprotein B antagonist on prion conversion is studied through the ability of apolipoprotein B antagonist to inhibit the prion replication ability of prion infection sensitive N2a cell lines.

a) N2a Cell Preparation:

Sub-clones of the parental mouse neuroblastoma N2a cell line are derived from single cells by limit dilution. A growing culture (Dulbecco's Modified Eagles Medium (DMEM Gibco # 41966-029), containing 10% fetal calf serum (FCS) and supplemented with 2 mM, L-glutamate and standard antibiotics (penicillin and streptomycin)) is diluted to a density of 5 cells/ml and 100 μl is transferred to individual wells of a 96 well plate and cultured for 1 week.

The individual cultures are examined microscopically to determine those wells which contained a single focus of growing cells. The single cell derived cultures are then transferred to 24 well plates and serially passaged every 3-4 days at 1:15 dilution to maintain stocks. A total of 63 cultures are isolated and all tested for sensitivity to infection by the RML strain of $PrP^{Sc}$. To do this, 4 μl of a 10% late stage infected brain extract is added per well of newly passaged cells, and the cultures are left for a further 4 days to reach 100% confluence. Cells were serially passaged thereafter in the absence of $PrP^{Sc}$. Tests showed that all trace of the initial innoculum disappeared by passage 4.

At this and later passages individual cultures are tested for the presence of $PrP^{Sc}$.

b) Prion Infection Resistant Cell Isolation by Cell Culture Dot Blotting:

The presence of $PrP^{Sc}$ in the 63 individual cell cultures is tested by cell culture dot blotting procedure in which lysis and proteinase K (PK) digestion are carried out directly in the culture dish. PK resistant $PrP^{Sc}$ is detected by dot blotting to PVDF membranes and exposure to anti-PrP antibody as follows:

Infected cells are grown for 3-4 days in 24-well plates and washed once with PBS. 40 μl DNase1 (1000 U/ml in H20) is added to each well at room temperature for 5 min, followed by 40 μl proteinase K solution (20 μg/ml in 100 mM Tris/HCl pH 7.4, 300 mM NaCl, 1% Triton-X100, 1% sodium deoxycholate). Plates are incubated at 37° C. for 1 hr with gentle agitation. Proteinase K digestion is stopped by addition of 2 μl of a solution containing 80 μg/ml PMSF, 10 mm Tris-HCl pH 8.0 and 1 mg/ml bromophenol blue. 20 μl aliquots are spotted onto PVDF membranes equilibrated with a degasses solution containing 192 mM Glycine, 25 mM Tris, 20% methanol. Membranes are then transferred to 3M guanidine Thiocyanate, 10 mM Tris HCL pH 8.0 for 10 min to denature proteins, rinsed in water and processed as for Western blotting using anti-PrP 6H4 (Prionics). Non-specific binding is blocked by incubation with 5% milk dissolved in PBS for 1 hr. The membrane is then exposed to specific primary antibody anti-PrP 6H4, followed by HRP-conjugated secondary antibody each diluted as appropriate in PBS, 0.3% Tween 20. Western blots are developed by ECL™ (Amersham) as directed according to the provider instructions.

The chemiluminescence signal from membranes is then analyzed directly using the Kodak Imagestation 440CF. The luminescence signal in each condition was normalized for possible differences in cell growth. Total protein content of a parallel lysate untreated with proteinase K is determined using the BCA assay (Biorad) and results are expressed as intensity/μg protein.

Of the 63 sub-clones analysed, 9 were found to be capable of replicating $PrP^{Sc}$, albeit with differing efficiencies (FIG. 3). The remaining 54 sub-clones were resistant to infection. The most highly prion infection sensitive cell lines were selected for further study together with several prion infection resistant sub-clones with similar morphologies and doubling times. We have have selected two of these cell lines: #23, a prion infection resistant clone, and #60 a prion infection sensitive clone.

These two cell lines have been maintained in culture for over 1 year and have been infected with RML in many different occasions throughout this period: on every occasion sub-clone #60 was highly infectable whereas sub-clone #23 was totally resistant. Prion infection sensitive sub-clones could be maintained as a chronically infected cell culture by serial passaging at 1:15 or 1:20 dilution every 3 or 4 days respectively.

No evident morphological differences by microscopy were observed between the resistant or sensitive cells or between non-infected and infected cells.

To validate the clinical relevance of this cellular model of PrP relication, exacts of chronically infected N2a cells, or buffer alone, were injected into the hippocampus of normal mice by stereotactic injection. Injection of N2a extracts resulted in onset of clinical symptoms of scrapie after 140 days and premature death whereas mock injection had no effect on mouse physiology or life span. This indicates that the cell based model for prion replication using prion infection sensitive N2a cells generates infectious PrP scrapie, confirming that the conversion of PrP in cells is a good model for the process which occurs in vivo.

c) Lipid Rafts Isolation:

Procedures for isolating lipid rafts based on resistance to solubilization in cold Triton X-100 followed by flotation on sucrose gradients have been described by numerous laboratories (Simons et al., 2000; Hooper et al., 1999). Lipid rafts from the two cell lines selected above are carried out as follows:

Subconfluent cultures of N2a cells are washed in PBS and collected by centrifugation 1000×g for 5 min. Typically 3×15 cm dishes are pooled equivalent to approximately $8\times10^7$ cells. The cell pellet is re-suspended in 1 ml ice cold raft buffer (1% Triton in PBS, containing 10 μM copper sulphate and a cocktail of complete protease inhibitors (Boehringer)). Cells are disrupted by seven passages through a 22G needle followed by incubation for 30 min at 4° C. with gentle agitation 2 volumes 60% sucrose in PBS is added and the lysate is transferred to a SW41 centrifuge tube. The lysate is carefully overlaid with 7 ml 35% sucrose and 1 ml 15% sucrose both in PBS and centrifuged 20 hr at 35,000 RPM. The lipid rafts are recovered in the top 1 ml of the gradient. Membranes are concentrated by addition of 10 volumes cold PBS and centrifugation at 100,000 g for 2 hr. Alternatively for 2D gel electrophoresis, proteins from the lipid raft fraction are recovered by precipitation in the presence of 5 vol acetone for 2 hr at −80° C. Acetone precipitates are collected by centrifugation 14000 g 20 min and washed twice in 70% ethanol.

In both sensitive and resistant cells around 1-2% of protein in the total lysate is recovered in the bouyant raft fraction. As shown by Western blotting (FIG. 4A) while PrP is barely detectable in the total cell extract, it is highly enriched in rafts leaving the sample layer totally depleted of PrP following centrifugation.

Figure 4:
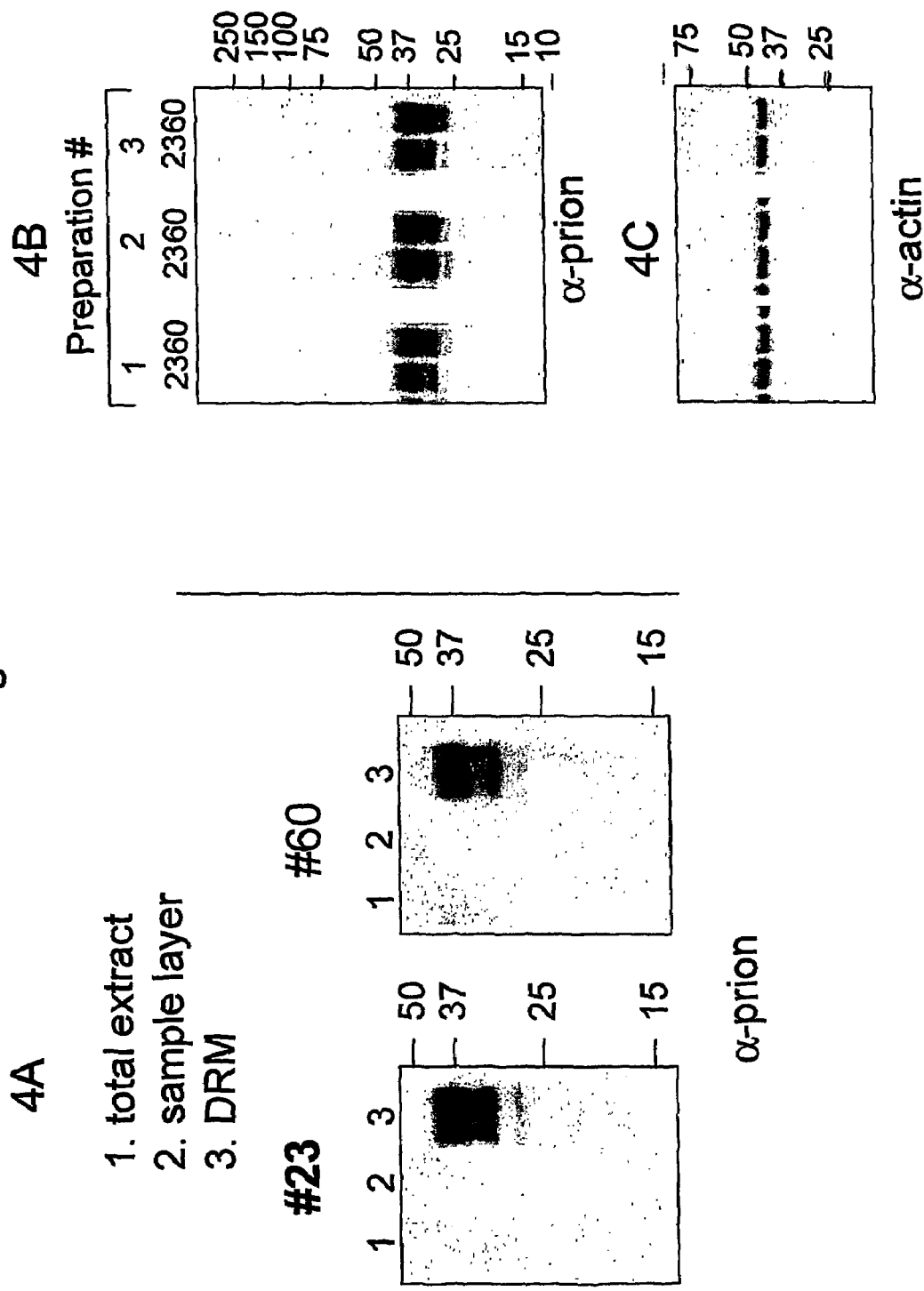

Prion infection sensitive clone #60 and the prion infection resistant clone #23 are compared by western blotting with anti-PrP (FIG. 4B). Three different independent pairs of raft preparations each containing 5 μg total raft proteins are re-probed with anti-actin antibody which confirms the uniformity of PrP protein loading (FIG. 4C).

The results indicate that the level of PrP in the lipid raft preparations from the two cell types is indistinguishable. Moreover the distribution between non-glycosylated mono- and di-glycosylated isoforms as well as the segregation to the detergent resistant membrane fraction shown in FIG. 4A is identical suggesting that none of these factors are likely to be responsible for the differing phenotypes.

PrP cDNA was amplified by RT-PCR from both cell lines as follows: Total RNA of N2a cells is prepared busing Trizol (Gibco) and the mouse PrP cDNA is reversed transcribed with Omniscript (Qiagen) using the protocol supplied by the manufacturer. The specific primer for cDNA synthesis is 5' TCAATTGAAAGAGCTACAGGTG 3' (SEQ ID NO: 4). The prion cDNA is amplified using standard PCR conditions in the presence of primers 5' ACCAGTCCAATTTAG-GAGAGCC 3' (SEQ ID NO: 5) (top strand) and 5' AGAC-CACGAGAATGCGAAGG 3' (SEQ ID NO: 6) (bottom strand). The PCR product was completely sequenced in the automated ABI3700 using the reagents and the protocol supplied by the manufacturer.

These data revealed that PrP mRNA is wild type in both cases and that both carry a Methionine at position 129, which in humans is the site for a frequent polymorphism.

Therefore, the expression levels, glycosylation patterns, intracellular localisation and primary sequences of $PrP^C$ in both cell types is indistinguishable and thus that other cellular factors are responsible for the differential response to $PrP^{Sc}$.

d) In vitro Cyclic Amplification of Protein Misfolding (PMCA) in Lipid Rafts from Prion Infection Sensitive Cells:

Lipid rafts obtained at §c are isolated from prion infection sensitive sub-clones, #60 sub-clones, collected by centrifugation as described above and re-suspended in PMCA conversion buffer at a concentration of 2-2.5 mg/ml (PBS containing final concentration of 300 mM NaCl, 0.5% Triton X100, 0.05% SDS).

A 10% extract of RML-infected mouse brain homogenate is added directly to the rafts preparation at a dilution of 1:100 based on protein content and aliquots of the mixture are either frozen immediately, incubated for 15 hr at 37° C. or subjected to 15 cycles of PMCA (5×0.1 second pulses of sonication followed by incubation at 37° C. for 1 hr).

Figure 5:
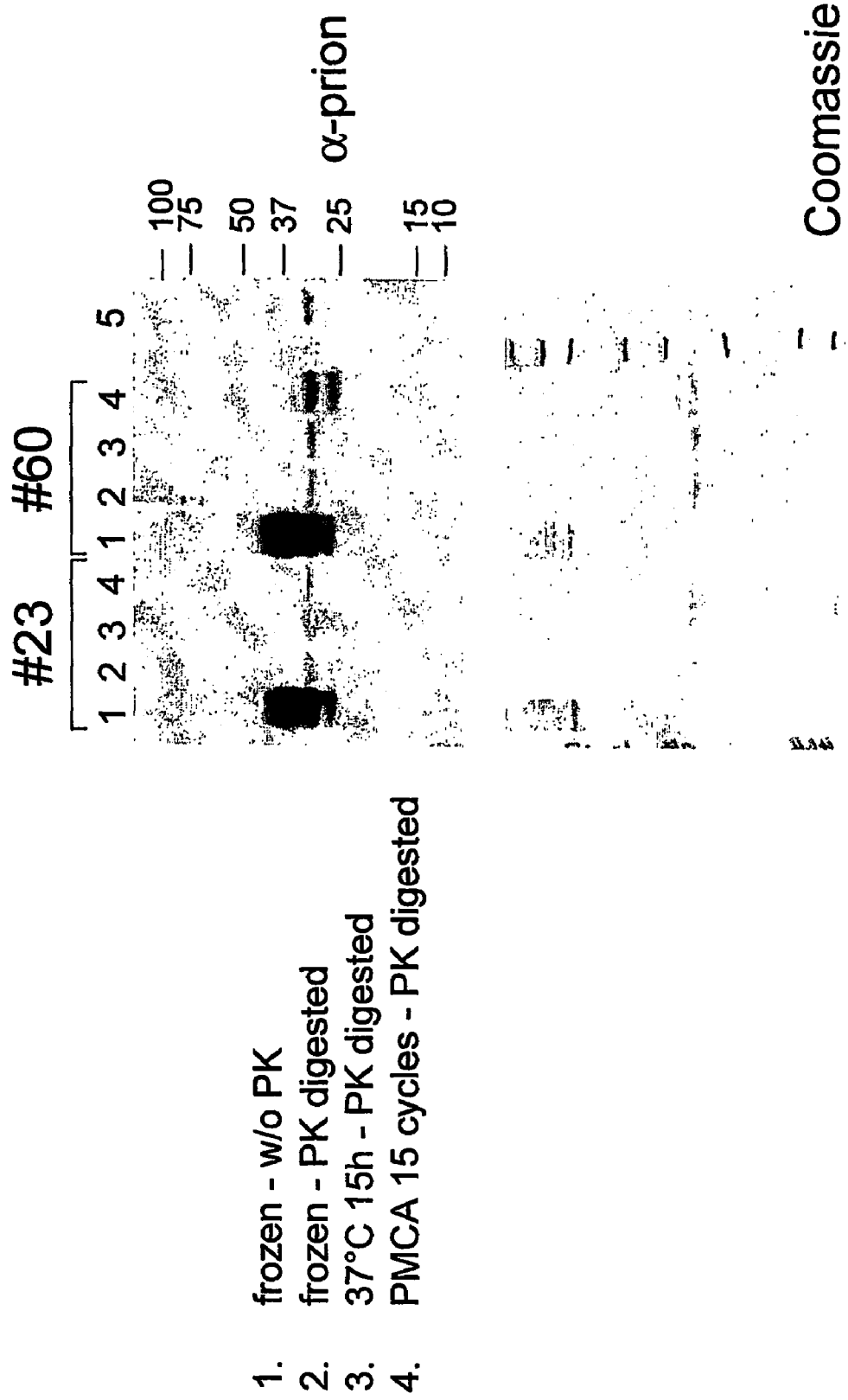

Aliquots of 20 μl sample are then treated with 10 μg/ml Proteinase K for 1 hr at 37° C. Lipids are removed by precipitating PK-resistant proteins with 5 vol acetone for 2 hr at −80° C. Acetone precipitates are collected by centrifugation 14000 g 20 min, washed twice in 70% ethanol analysed by Western blotting with 6H4 anti-PrP (FIG. 5).

Compared to the mixture without PK treatment (lanes 1 and 5) all digested samples show a shift in molecular weight characteristic of the N-terminally truncated PK resistant form $PrP_{27-30}$. It should be noted that the 6H4 antibody also has low level cross reactivity with PK which migrates at 30 kDa, close to the di-glycosylated form of PK-digested PrP. Analysis of the data with this in mind shows that the initial level of PK-resistant PrP derived from the diluted brain extract, which is present in the non-amplified mixtures, is barely detectable under these conditions (lanes 2).

A slight increase in signal is seen when the prion infection sensitive (#60) DRM is incubated at 37° C. for 15 hr (lane 3 from #60), however the most dramatic increase in PK-resistant PrP is seen when this sample is subjected to 15 cycles of PMCA (lane 4 from #60). This indicates that all factors required for conversion of $PrP^C$ to $PrP^{Sc}$ are resident in the lipid rafts from the prion infection sensitive N2a cells. Interestingly, in the parallel analysis in which the DRM from the prion infection resistant cell line #23 was used, no amplification in vitro was observed (lane 4 from #23) indicating that the capacity of the lipid rafts to convert the prion protein in vitro reflects the activity observed in the intact cells.

e) Effect of Antibody Raised Against Apolipoprotein B on Prion Replication by Prion Infection Sensitive N2a Cells:

Chronically infected sensitive cells were cultured in 24-well dishes in the presence of a goat polyclonal antibody raised against human Apo B (Chemicon) at increasing concentrations from 0 to 2 mg/ml in DMEM Gibco # 41966-029, containing 1×B27 supplements (Gibco #17504-044) and standard antibiotics (penicillin and streptomycin)

A parallel series of cultures was incubated in the presence of the same concentration range of total IgG from a naïve goat. The results show that concentrations of anti-hApoB antibody above 0.5 mg/ml result in progressive inhibition of PrP replication as revealed by quantitative dot blotting (FIG. 6).

These data show the role of Apolipoprotein B in the prion conversion.

Example 3

Proteomics Analysis of Lipid Rafts of Prion Infection Resistant and Sensitive Cells Since the two cell preparations are indistinguishable in terms of their PrP content a more complete protein comparison using 2D gel electrophoresis was performed to show differences in other proteins that might underline the difference in conversion activity between the two sub-clones.

2D gel preparations are prepared as follows:

Acetone precipitated proteins (see §c) are re-suspended in 20 μl 1% SDS, 0.23% DTT and heated to 95° C. for 5 min. After the preparation is cooled to room temperature, 25 μl of a solution (9M urea, 4% CHAPS, 65 mM DTT, 35 mM Tris base) is added.

Fifteen minutes later, 85 μl of a solution containing 7M urea, 2M thiourea, 4% CHAPS, 100 mM DTT is further added to the mixture. After a further 15 min, non-solubilized material is removed by centrifugation at 14000 RPM during 5 min and the supernatant is applied directly to a 7 cm IPG strip and left to re-hydrate overnight. For IEF the voltage is progressively increased from 300V to 3.5 kV and electrophoresed for a total of 20 kVh. Proteins are resolved in the second dimension using single well 4-12% gradient gels (Novex) and stained using the silver express kit (Invitogen) according to the instructions supplied.

Analysis by 2D gels reveals the fraction of protein that is recovered in the lipid rafts (approximately 1-2% protein in the N2a cell lysate) as a reproducible subset of total cell proteins in which several hundred species can be visualized following silver staining (FIGS. 7A and B).

The 2D patterns are compared between preparations isolated from the prion infection sensitive and resistant cells. The analysis is focused on several proteins identified in the basic range of the gel which are more abundant in DRMs from prion infection resistant cells (arrows in FIGS. 7C and D).

Following preparative scale electrophoresis, the two proteins indicated by arrows are excised and processed for MS sequencing. From both proteins an identical tryptic peptide is found with a monoisotopic mass of 1234.6. The N-terminal sequence of this tryptic peptide is: ENFAGEATLQR (SEQ ID NO: 3). All amino acids in the peptide are identified in the MS/MS spectrum of doubly charged precursor ion at m/z 618.30 And through its Mascot analysis.

Database searching identified this protein unambiguously as Apolipoprotein B (Apo B). Since the molecular weight of fall length Apo B is in excess of 500 kDa while these two spots migrate with estimated molecular weights of 40 kDa and 30 kDa, we presume that the latter are fragments generated either in the cell or during sample preparation. The sequence corresponds to amino acids 3548-3558 of the human Apo B protein, which is present only in ApoB-100 and not in the truncated ApoB-48 form.

These data suggest that fragments of a molecular weight of or about 30 to 40 kDa comprising the sequence of SEQ ID NO: 3 may have a role in the prion conversion pathway.

Example 4

Binding and Internalisation of Fluorescent LDL Receptor by Resistant and Sensitive Cells N2a subclones #23 (prion infection sensitive) and #60 (prion infection resistant) were cultured in 24 well plates in standard DMEM medium containing 10% FCS for 2 days then transferred to the same medium (300 µl) containing 1% FCS for 1 hr. To visualize cell surface binding, plates were placed on ice to inhibit endocytosis and 3 µl fluorescent DiI-LDL (Molecular Probes) was added for 30 min.

LDL-binding was visualized by fluorescence microscopy. To study LDL uptake by each of the sub-clones, cells were incubated at 37 C with 3 µl DiI-LDL for 2 h prior to microscopic examination.

Control cultures were incubated in parallel with DiI-coupled acetylated LDL which does not bind the LDL receptor or with Hoechst to visualize cell nuclei.

The binding or uptake of fluorescent DiI-LDL is similar for prion infection resistant and prion infection sensitive cells, suggesting that the level of the LDL receptor between these two cell types is similar.

REFERENCES

Aizawa et al., Brain R. 768 (1-2), 208-14, 1997;
Baron et al., The EMBO Journal, 21, 5, 1031-1040, 2002;
Baumann et al., Biochem J., 349, 77-8, 2000;
Bruce et al., Nature, 389, 498-501, 1997;
Bueler et al., Cell 73, 1339-1347, 1993;
Chabry et al., J. Biol. Chem. 273, 13203-13207, 1998;
Choe et al., Electrophoresis, 23, 2242-2246, 2002;
Choi et al., J. Lip. Res., 38(1)77-85, 1997;
Clavey et al., Annales d'Endocrinologie, 52, 459-463, 1991;
Cohen et al., Ann. Rev. Biochem. 67, 1998;
Dietrich et al., Journal of virology, 65(9), 4759-476, 1991;
Enari et al., Proc. Natl. Acad. Sci. USA 98, 9295-9299, 2001;
Fantini et al., Expert Reviews in Molecular Medicine, Dec. 20, 1-22, 2002;
Golaz et al., Electrophoresis, 16, 1184-118, 1995;
Hooper et al., Mol. Memb. Biol. 16, 145-156, 1999;
Lehninger et al., Principles of Biochemistry, 2nd Ed. New York: Worth Publishers, 1993;
Lucassen et al., Biochemistry, 42, 4127-4135, 2003;
Pan et al., Proc. Natl. Acad. Sci. (USA) 90, 10962-10966, 1993;
Prusiner, Science 252, 1515-1522, 1991;
Prusiner, Proc. Natl. Acad. Sci. USA 95, 13363-13383, 1998;
Roos et al., Brain 96, 1-20, 1973;
Saborio et al., Biochem. Biophys. Res. Commun. 258, 470-475, 1999;
Saborio et al., Nature 411, 810-813, 2001;
Schulz et al., American Journal of Pathology, 156(1), 51-56, 2000;
Segrest et al., Journal of Lipid Research, 42, 1346-1367, 2001;
Simons et al, Molecular Cell Biology 1, p 3141, 2000;
Scott et al., Proc. Natl. Acad. Sci. USA 96, 15137-15142, 1999;
Soto et al., Trends Mol. Med. 7, 2001;
Taraboulos at al., The Journal of Cell Biology, 129 (1), 121-132, 1995;
Telling et al., Proc. Natl. Acad. Sci. USA 91, 9936-9940, 1994;
Tsui-Pierchala et al., Trends Neurosci. 25, 2002;
Wang et al., Aeterioscler. Thromb. Vas. Biol., 20(5), 1301-8, 2000;
Will et al., Lancet 347, 925, 1996;
Yamada et al, Ann Clin. Lab. Sci. 27(4), 77-85, 1997;
U.S. Pat. No. 5,134,121;
U.S. Pat. No. 5,276,059;
U.S. Pat. No. 5,948,763;
U.S. Pat. No. 6,022,683;
U.S. Pat. No. 6,197,972;
U.S. Pat. No. 6,355,610;
U.S. Pat. No. 6,552,922;
US 20020128175;
US 20020155426;
WO 97/14437;
WO 99/15159;
WO 0168710;
WO 0204954;
WO 02065133;
WO 03002533;
WO 03005037;
WO 03045921;
WO 2004043403.

The invention claimed is:

1. A method for the detection of a prion disease within a subject suspected of suffering from such a disease, the method comprising:
   (i) contacting a sample from said subject with Apolipoprotein B or a peptide fragment thereof;
   (ii) contacting the preparation obtained in step (i) with $PrP^C$ or a $PrP^C$ containing mixture; and
   (iii) determining the presence and/or an amount of $PrP^{Sc}$ in said sample;
   wherein the presence of $PrP^{Sc}$ in said sample is indicative of the presence of prions in said subject.

2. The method of claim 1, wherein the prion disease is bovine spongiform encephalopathy (BSE).

3. The method of claim 1, wherein the prion disease is a Creutzfeld-Jacob disease.

4. A method for the detection of $PrP^{Sc}$ within a sample, comprising:
   (i) contacting said sample with Apolipoprotein B or a peptide fragment thereof;
   (ii) contacting the sample obtained in (i) with $PrP^C$ or a $PrP^C$ containing mixture; and
   (iii) determining the presence and/or an amount of $PrP^{Sc}$ in said sample,
   wherein the presence of $PrP^{Sc}$ indicates that the sample contains $PrP^{Sc}$.

5. A method for identifying, in a sample, a compound which modulates the transition of $PrP^C$ into $PrP^{Sc}$, comprising:
   (i) contacting said sample with Apolipoprotein B or a peptide fragment thereof; in the presence of said modulatory compound and (b) in the absence of said compound;
   (ii) contacting the preparation obtained in step (i) a and (i) b with $PrP^C$ or a $PrP^C$ containing mixture; and
   (iii) determining the amount of $PrP^{Sc}$ (a) in the presence of said modulatory compound and (b) in the absence of said modulatory compound,
   wherein the presence of $PrP^{Sc}$ identifies a compound that modulates the transition of $PrP^C$ into $PrP^{Sc}$.

6. The method of claim 1, wherein the peptide or the protein contains the sequence of SEQ ID NO: 3.

7. The method of claim 1, wherein the peptide or the protein has a molecular weight from 30 and 40 kDa and has a sequence selected from the group of Apolipoprotein B between positions 3201-3558, 3548-3905, 3201-3905, 3291-3558, 3548-3815, and 3291-3815.

8. The method of claim 1, wherein the protein is Apolipoprotein B or a fragment thereof consisting of a peptide fragment of Apolipoprotein B between positions 3201-3558, 3548-3905, 3201-3905, 3291-3558, 3548-3815, or 3291-3815.

9. The method of claim 1, wherein the peptide or the protein forms a complex with a LDL receptor.

10. The method of claim 1, wherein the peptide or the protein contains the sequence of SEQ ID NO: 3.

11. The method of claim 1, wherein the peptide or the protein has a molecular weight from 30 and 40 kDa and is a fragment of Apolipoprotein B comprising the consecutive amino acid residues between positions 3201-3553, 3548-3905, 3201-3905, 3291-3558, 3548-3815, or 3291-3815.

12. The method of claim 4, wherein the protein is Apolipoprotein B or a fragment thereof consisting of a peptide fragment of Apolipoprotein B between positions 3201-3558, 3548-3905, 3201-3905, 3291-3558, 3548-3815, or 3291-3815.

13. The method of claim 4, wherein the peptide or the protein from a complex wit a LDL receptor.

14. The method of claim 4, wherein the peptide or the protein contains the sequence of SEQ ID NO: 3.

15. The method of claim 4, wherein the peptide or the protein has a molecular weight from 30 and 40 kDa and is a fragment of Apolipoprotein B comprising the consecutive amino acid residues between positions 3201-3558, 3548-3905, 3201-3905, 3291-3558, 3548-3815, or 3291-3815.

16. The method of claim 4, wherein the sample is obtained from a subject suspected of having a prion disease selected from the group consisting of bovine spongiform encephalopathy (BSE) and Creutzfeld-Jacob Disease (CJD).

17. The method of claim 5, wherein the protein is Apolipoprotein B or a fragment thereof consisting of a peptide fragment of Apolipoprotein B between positions 3201-3558, 3548-3905, 3201-3905, 3291-3558, 3548-3815, or 3291-3815.

18. The method of claim 5, wherein the peptide or the protein forms a complex with a LDL receptor.

19. The method of claim 5, wherein the peptide or the protein contains the sequence of SEQ ID NO: 3.

20. The method of claim 5, wherein the peptide or the protein has a molecular weight from 30 and 40 kDa and is a fragment of Apolipoprotein B comprising the consecutive amino acid residues between positions 3201-3558, 3548-3905, 3201-3905, 3291-3558, 3548-3815, or 3291-3815.

21. The method of claim 5, wherein the sample is obtained from a subject suspected of having a prion disease selected from the group consisting of bovine spongiform encephalopathy (BSE) and Creutzfeld-Jacob Disease (CJD).

22. The method of claim 5, wherein determining the amount of $PrP^{Sc}$ in the sample comprises performing a protein misfolding cyclic amplification (PMCA) assay.

23. The method of claim 22, wherein the sample is a normal brain homogenate containing $PrP^C$ and substrate.

24. The method of claim 22, wherein the sample is lipid rafts from an infection-sensitive neuroblasma cell line N2a containing $PrP^C$ and substrate.

25. The method of claim 5, which comprises determining the amount of $PrP^{Sc}$ in the sample by performing a protein misfolding cyclic amplification assay (PMCA); and
   wherein the protein is Apolipoprotein B, and
   wherein the sample is lipid rafts from infection sensitive neuroblasma cell line N2a that contain normal $PrP^C$ and substrate.

26. The method of claim 5, wherein said modulatory compound is an antagonist of Apolipoprotein B.

27. The method of claim 5, wherein said modulatory compound is an antibody that binds to Apolipoprotein B.

28. The method of claim 5, wherein said modulatory compound is a LDL-receptor antagonist.

29. A method for the detection of $PrP^{Sc}$ in a biological sample comprising:
   (i) contacting a sample from a subject exposed to a prion with Apolipoprotein B or a peptide fragment thereof;
   (ii) contacting the preparation obtained in step (i) with $PrP^C$ or $PrP^C$ containing mixtures; and
   (iii) determining the presence and/or an amount of $PrP^{Sc}$ in said sample,
   wherein the presence of $PrP^{Sc}$ in said sample is indicative of the presence of prions in the sample.

30. The method of claim 29, wherein said subject is human and has, or is at risk of developing, vCJD.

* * * * *

UNITED STATES PATENT AND TRADEMARK OFFICE
CERTIFICATE OF CORRECTION

| | | |
|---|---|---|
| PATENT NO. | : 7,598,046 B2 | Page 1 of 1 |
| APPLICATION NO. | : 10/560978 | |
| DATED | : October 6, 2009 | |
| INVENTOR(S) | : Soto-Jara et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 234 days.

Delete the phrase "by 234 days" and insert -- by 525 days --

Signed and Sealed this

Twenty-fifth Day of May, 2010

David J. Kappos
*Director of the United States Patent and Trademark Office*